(12) United States Patent
Ohrui et al.

(10) Patent No.: US 8,034,944 B2
(45) Date of Patent: Oct. 11, 2011

(54) BENZOFLUORANTHENE COMPOUND AND ORGANIC LIGHT-EMITTING DEVICE USING THE COMPOUND

(75) Inventors: Hiroki Ohrui, Kawasaki (JP); Akihito Saitoh, Yokohama (JP); Chika Negishi, Yokosuka (JP); Hironobu Iwawaki, Yokohama (JP); Masanori Muratsubaki, Hachioji (JP); Hiroyuki Tomono, Tokyo (JP); Tetsuya Kosuge, Kawasaki (JP); Akihiro Senoo, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 482 days.

(21) Appl. No.: 12/296,058

(22) PCT Filed: Dec. 12, 2007

(86) PCT No.: PCT/JP2007/075231
§ 371 (c)(1),
(2), (4) Date: Oct. 3, 2008

(87) PCT Pub. No.: WO2008/078824
PCT Pub. Date: Jul. 3, 2008

(65) Prior Publication Data
US 2009/0278118 A1 Nov. 12, 2009

(30) Foreign Application Priority Data
Dec. 26, 2006 (JP) .................................. 2006-349579

(51) Int. Cl.
*C07D 215/06* (2006.01)
*H01L 51/50* (2006.01)

(52) U.S. Cl. .......... 546/152; 313/504; 428/917; 546/75; 546/79; 546/102; 546/111; 546/139

(58) Field of Classification Search .................. 546/152, 546/139, 102, 79, 75, 111; 428/917; 313/504
See application file for complete search history.

(56) References Cited

U.S. PATENT DOCUMENTS

| | | | |
|---|---|---|---|
| 7,097,917 B1 | 8/2006 | Fujita et al. | 428/690 |
| 2007/0072002 A1* | 3/2007 | Kim et al. | 428/690 |
| 2007/0249878 A1 | 10/2007 | Iwawaki et al. | 585/27 |
| 2007/0252141 A1 | 11/2007 | Negishi et al. | 257/40 |
| 2008/0124577 A1 | 5/2008 | Saitoh et al. | 428/704 |

FOREIGN PATENT DOCUMENTS

| | | |
|---|---|---|
| JP | 10-189247 | 7/1998 |
| JP | 10-294179 | 11/1998 |
| JP | 2000-311786 | 11/2000 |
| JP | 2001-160489 | 6/2001 |
| JP | 2002-069044 | 3/2002 |
| JP | 2003-026616 | 1/2003 |
| JP | 2003-212875 | 7/2003 |
| JP | 2005-068087 | 3/2005 |
| JP | 2005-068367 | 3/2005 |
| JP | 2006-016363 | 1/2006 |
| WO | 2008/016166 A1 | 2/2008 |

OTHER PUBLICATIONS

Eckert et al., "Synthesis of Polycylic Aromatic Heterocyclic Compounds Via Thermal Isomerizations of 1, 8-Diarylethynylnaphthalenes," *Monatshefte fur Chemie*, vol. 129, No. 10, 1035-1048 (1998).

Jaung et al., "Syntheses and Spectral Properties of New Dicyanopyrazine-related Heterocycles from Diaminomaleonnitrile," *Journal of Chemical Research, Synopses*, No. 6, 1301-1323 (1998).

Korean Office Action issued in the counterpart application No. 10-2009-7015427 dated Apr. 22, 2011—5 pages.

* cited by examiner

*Primary Examiner* — Charanjit Aulakh
(74) *Attorney, Agent, or Firm* — Fitzpatrick, Cella, Harper & Scinto

(57) ABSTRACT

There are provided a novel benzofluoranthene compound and an organic light-emitting device which uses the benzofluoranthene compound, gives a blue emission hue with extremely good purity, and has an optical output with a high efficiency, a high luminance, and a long life. Specifically, there are provided a benzofluoranthene compound represented by the general formula shown below and an organic light-emitting device including a pair of electrodes including an anode and a cathode one of which is a transparent or translucent electrode material, and an organic compound layer disposed between the pair of electrodes and including a material for an organic light-emitting device containing the benzofluoranthene compound.

(1)

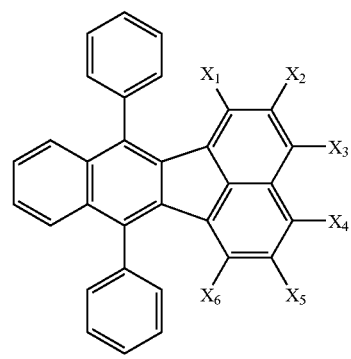

In the general formula (1), one of $X_1$, $X_2$, $X_3$, $X_4$, $X_5$, and $X_6$ represents a substituted or unsubstituted fused heterocyclic group having four or less rings, and the others of $X_1$, $X_2$, $X_3$, $X_4$, $X_5$, and $X_6$ each represent a hydrogen atom.

6 Claims, 5 Drawing Sheets

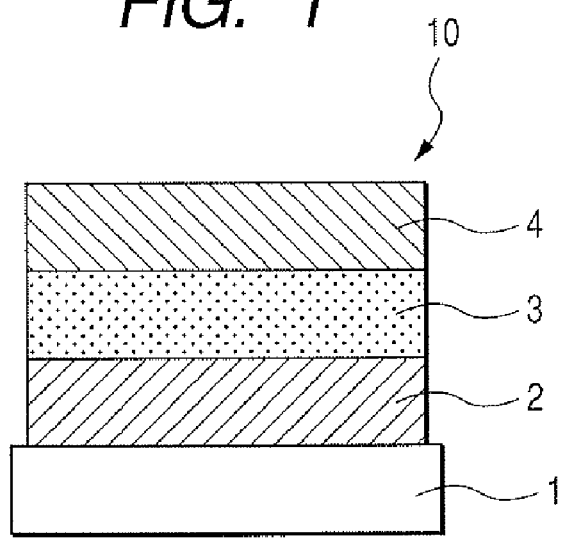
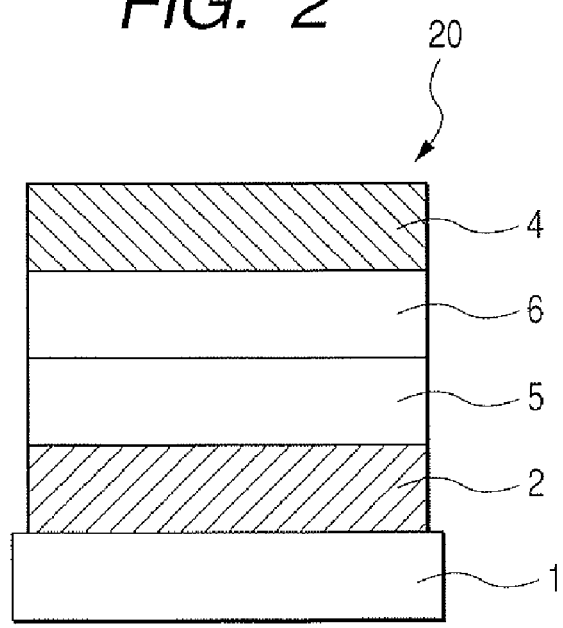

BENZOFLUORANTHENE COMPOUND AND ORGANIC LIGHT-EMITTING DEVICE USING THE COMPOUND

TECHNICAL FIELD

The present invention relates to a benzofluoranthene compound and an organic light-emitting device using the compound.

BACKGROUND ART

An organic light-emitting device is a device having a thin film which contains a fluorescent or phosphorescent organic compound and is interposed between electrodes. Electrons and holes (positive holes) are injected from the respective electrodes, whereby excitons of the fluorescent or phosphorescent compound are produced. The excitons radiate light upon return thereof to a ground state. Recent progress of an organic light-emitting device is remarkable, and the characteristics of the device enable a thin and light weight light-emitting device with a high luminance at a low applied voltage, a variety of emission wavelengths, and a high-speed responsibility. From this fact, it is suggested that the device have potential to find use in a wide variety of applications.

However, in the present circumstances, an optical output with a higher luminance or a higher conversion efficiency is needed. In addition, the organic light-emitting device still involves a large number of problems in terms of durability such as a change over time due to long-term use and degradation due to an atmospheric gas containing oxygen, moisture or the like. Further, when the application of the device to a full-color display or the like is taken into consideration, the emission of blue, green, or red light with good color purity is needed. However, these problems have not been sufficiently solved yet.

Meanwhile, a benzofluoranthene compound has been proposed as a blue-light-emitting material. Organic light-emitting devices using a benzofluoranthene compound as a light-emitting material have been disclosed in Japanese Patent Application Laid-Open Nos. H10-294179, 2002-69044, 2003-26616, and 2005-68087. However, it is difficult to say that those organic light-emitting devices have sufficient life characteristics. In particular, when one attempts to apply those devices to a full-color display, the compound cannot be employed as a blue-light-emitting material which can satisfy demands for satisfactory emission efficiency, durability life, and color purity.

DISCLOSURE OF THE INVENTION

The present invention has been accomplished with a view to solving such problems of the background art.

That is, an object of the present invention is to provide an organic light-emitting device which shows a blue emission hue with extremely good purity and has an optical output with a high efficiency, a high luminance, and a long life.

Further, another object of the present invention is to provide a benzofluoranthene compound which is used as a material for an organic light-emitting device.

Moreover, still another object of the present invention is to provide an organic light-emitting device that can be easily produced at a relatively low cost.

The inventors of the present invention have made extensive studies with a view to solving the above-mentioned problems and have accomplished the present invention. That is, the present invention provides a benzofluoranthene compound represented by the following general formula (1):

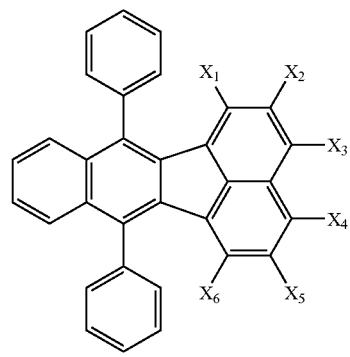

(1)

wherein one of $X_1$, $X_2$, $X_3$, $X_4$, $X_5$, and $X_6$ represents a substituted or unsubstituted fused heterocyclic group having four or less rings, and the others of $X_1$, $X_2$, $X_3$, $X_4$, $X_5$, and $X_6$ each represent a hydrogen atom.

In the material for an organic light-emitting device of the present invention, by incorporating a single fused heterocyclic ring having four or less rings at any specified position of the 1- to 6-positions of a benzofluoranthene skeleton, a stable amorphous film can be formed which exhibits excellent electron-transporting property. Further, the incorporation at the specified position of a single fused heterocyclic ring having four or less rings, not two or more fused heterocyclic rings each having four or less rings, can not only control thermal decomposition of the material at the time of sublimation to thereby suppress reduction in sublimation property of the material but also cause the material to maintain an appropriate hole conduction level and an appropriate electron conduction level for a blue-light-emitting material. Therefore, according to the present invention, there can be provided an organic light-emitting device which emits blue light having good color purity with a high efficiency, and a benzofluoranthene compound which is used in the organic light-emitting device. In addition, the organic light-emitting device containing the benzofluoranthene compound of the present invention can emit light with a high luminance at a low applied voltage, and is excellent in durability.

Further feature of the present invention will become apparent from the following description of exemplary embodiments with reference to the attached drawings.

BRIEF DESCRIPTION OF THE DRAWINGS

FIG. 1 is a cross-sectional view illustrating a first embodiment of an organic light-emitting device of the present invention.

FIG. 2 is a cross-sectional view illustrating a second embodiment of the organic light-emitting device of the present invention.

BEST MODE FOR CARRYING OUT THE INVENTION

Figure 3:
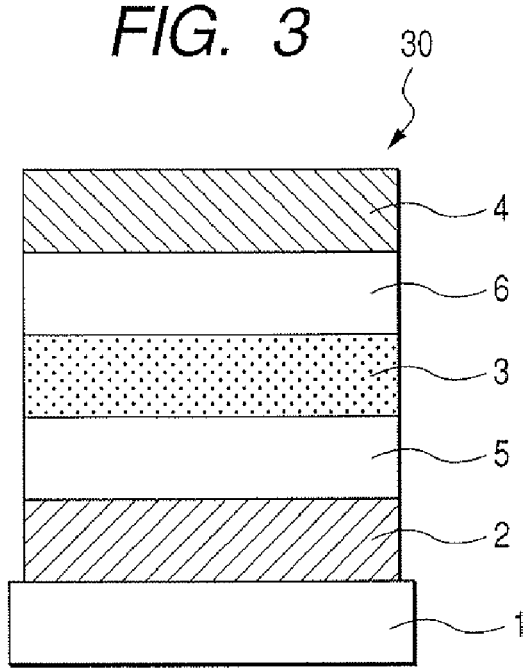
FIG. 3 is a cross-sectional view illustrating a third embodiment of the organic light-emitting device of the present invention.

Hereinafter, the present invention will be described in detail.

First, the benzofluoranthene compound of the present invention will be described. The application of the compound to a material for an organic light-emitting device as an example of a specific application will also be described.

The present invention relates to a benzofluoranthene compound represented by the following general formula (1).

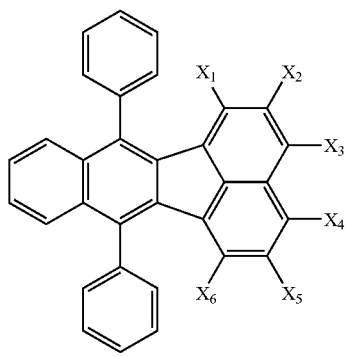

(1)

In the general formula (1), one of $X_1$, $X_2$, $X_3$, $X_4$, $X_5$, and $X_6$ represents a substituted or unsubstituted fused heterocyclic group having four or less rings, and the others of $X_1$, $X_2$, $X_3$, $X_4$, $X_5$, and $X_6$ each represent a hydrogen atom.

As the fused heterocyclic group having four or less rings, there is preferably included a substituent represented by the following general formula (2).

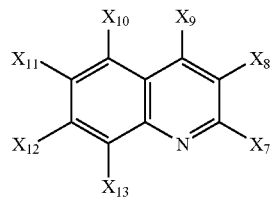

(2)

In the general formula (2), one of $X_7$, $X_8$, $X_9$, $X_{10}$, $X_{11}$, $X_{12}$, and $X_{13}$ represents a bond, the others of $X_7$, $X_8$, $X_9$, $X_{10}$, $X_{11}$, $X_{12}$, and $X_{13}$ each represent, independently of one another, a hydrogen atom or a substituent, and adjacent ones of $X_7$, $X_8$, $X_9$, $X_{10}$, $X_{11}$, $X_{12}$, and $X_{13}$ may be joined to form a ring.

The term "substituent" as herein employed refers to a halogen atom, a substituted or unsubstituted alkyl group, a substituted or unsubstituted aryl group, or a cyano group.

Examples of the halogen atom represented by $X_7$ to $X_{13}$ include fluorine, chlorine, bromine, and iodine.

Examples of an alkyl group represented by $X_7$ to $X_{13}$ include, but are of course not limited to, a methyl group, an ethyl group, an n-propyl group, an n-butyl group, an n-pentyl group, an n-hexyl group, an n-heptyl group, an n-octyl group, an n-decyl group, an iso-propyl group, an iso-butyl group, a sec-butyl group, a tert-butyl group, an iso-pentyl group, a neopentyl group, a tert-octyl group, a fluoromethyl group, a difluoromethyl group, a trifluoromethyl group, a 2-fluoroethyl group, a 2,2,2-trifluoroethyl group, a perfluoroethyl group, a 3-fluoropropyl group, a perfluoropropyl group, a 4-fluorobutyl group, a perfluorobutyl group, a 5-fluoropentyl group, a 6-fluorohexyl group, a chloromethyl group, a trichloromethyl group, 2-chloroethyl group, a 2,2,2-trichloroethyl group, a 4-chlorobutyl group, a 5-chloropentyl group, a 6-chlorohexyl group, a bromomethyl group, a 2-bromoethyl group, an iodomethyl group, a 2-iodoethyl group, a hydroxymethyl group, a hydroxyethyl group, a cyclopropyl group, a cyclobutyl group, a cyclopentyl group, a cyclohexyl group, a cyclopentylmethyl group, a cyclohexylmethyl group, a cyclohexylethyl group, a 4-fluorocyclohexyl group, a norbornyl group, and an adamantyl group.

Examples of an aryl group represented by $X_7$ to $X_{13}$ include, but are of course not limited to, a phenyl group, a 4-methylphenyl group, 4-ethylphenyl group, a 4-methoxyphenyl group, a 4-fluorophenyl group, a 4-trifluoromethylphenyl group, a 3,5-dimethylphenyl group, a 2,6-diethylphenyl group, a mesityl group, a 4-tert-butylphenyl group, a ditolylaminophenyl group, and a biphenyl group.

Examples of the substituents with which the above-mentioned alkyl group and aryl group may be substituted include, but are of course not limited to: alkyl groups such as a methyl group, an ethyl group, a propyl group, a tert-butyl group, and a trifluoromethyl group; aryl groups such as a phenyl group and a biphenyl group; alkoxy groups such as a methoxy group and an ethoxy group; halogen atoms such as fluorine, chlorine, bromine, and iodine; a hydroxyl group; a cyano group; and a nitro group.

Of the substituents represented by $X_7$ to $X_{13}$, adjacent ones may be joined to form a ring.

As the fused heterocyclic group having four or less rings, there is also preferably included a substituent represented by the following general formula (3).

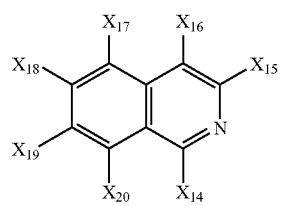

(3)

In the general formula (3), one of $X_{14}$, $X_{15}$, $X_{16}$, $X_{17}$, $X_{18}$, $X_{19}$, and $X_{20}$ represents a bond, the others of $X_{14}$, $X_{15}$, $X_{16}$, $X_{17}$, $X_{18}$, $X_{19}$, and $X_{20}$ each represent, independently of one another, a hydrogen atom or a substituent, and adjacent ones of $X_{14}$, $X_{15}$, $X_{16}$, $X_{17}$, $X_{18}$, $X_{19}$, and $X_{20}$ may be joined to form a ring.

The term "substituent" as herein employed refers to a halogen atom, a substituted or unsubstituted alkyl group, a substituted or unsubstituted aryl group, or a cyano group.

The halogen atom, the alkyl group, and the aryl group represented by $X_{14}$ to $X_{20}$, and the substituents with which the alkyl group and the aryl group may be substituted are as defined above for the substituents represented by $X_7$ to $X_{13}$ of the above general formula (2).

Of the substituents represented by $X_{14}$ to $X_{20}$, adjacent ones may be joined to form a ring.

As the fused heterocyclic group having four or less rings, there is also preferably included a substituent represented by the following general formula (4).

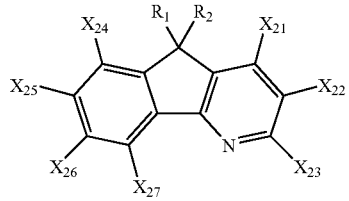

(4)

In the general formula (4), one of $X_{21}$, $X_{22}$, $X_{23}$, $X_{24}$, $X_{25}$, $X_{26}$, and $X_{27}$ represents a bond, and the others of $X_{21}$, $X_{22}$, $X_{23}$, $X_{24}$, $X_{25}$, $X_{26}$, and $X_{27}$ each represent, independently of one another, a hydrogen atom or a substituent.

The term "substituent" as herein employed refers to a halogen atom, a substituted or unsubstituted alkyl group, a substituted or unsubstituted aryl group, or a cyano group.

The halogen atom, the alkyl group, and the aryl group represented by $X_{21}$ to $X_{27}$, and the substituents with which the alkyl group and the aryl group may be substituted are as defined above for the substituents represented by $X_7$ to $X_{13}$ of the above general formula (2).

In the general formula (4), $R_1$ and $R_2$ each represent, independently of each other, a substituted or unsubstituted alkyl group.

Examples of an alkyl group represented by $R_1$ and $R_2$ include, but are of course not limited to, a methyl group, an ethyl group, an n-propyl group, an n-butyl group, an n-pentyl group, an n-hexyl group, an n-heptyl group, an n-octyl group, an n-decyl group, an iso-propyl group, an iso-butyl group, a sec-butyl group, a tert-butyl group, an iso-pentyl group, a neopentyl group, a tert-octyl group, a fluoromethyl group, a difluoromethyl group, a trifluoromethyl group, a 2-fluoroethyl group, a 2,2,2-trifluoroethyl group, a perfluoroethyl group, a 3-fluoropropyl group, a perfluoropropyl group, a 4-fluorobutyl group, a perfluorobutyl group, a 5-fluoropentyl group, a 6-fluorohexyl group, a chloromethyl group, a trichloromethyl group, 2-chloroethyl group, a 2,2,2-trichloroethyl group, a 4-chlorobutyl group, a 5-chloropentyl group, a 6-chlorohexyl group, a bromomethyl group, a 2-bromoethyl group, an iodomethyl group, a 2-iodoethyl group, a hydroxymethyl group, a hydroxyethyl group, a cyclopropyl group, a cyclobutyl group, a cyclopentyl group, a cyclohexyl group, a cyclopentylmethyl group, a cyclohexylmethyl group, a cyclohexylethyl group, a 4-fluorocyclohexyl group, a norbornyl group, and an adamantyl group.

Examples of the substituent with which the above-mentioned alkyl group may be substituted include, but are of course not limited to: alkyl groups such as a methyl group, an ethyl group, a propyl group, a tert-butyl group, and a trifluoromethyl group; aryl groups such as a phenyl group and a biphenyl group; alkoxy groups such as a methoxy group and an ethoxy group; halogen atoms such as fluorine, chlorine, bromine, and iodine; hydroxyl groups; cyano groups; and nitro groups.

As the fused heterocyclic group having four or less rings, there is also preferably included a substituent represented by the following general formula (5).

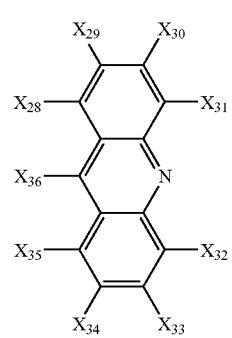

(5)

In the general formula (5), one of $X_{28}$, $X_{29}$, $X_{30}$, $X_{31}$, $X_{32}$, $X_{33}$, $X_{34}$, $X_{35}$, and $X_{36}$ represents a bond, and the others of $X_{28}$, $X_{29}$, $X_{30}$, $X_{31}$, $X_{32}$, $X_{33}$, $X_{34}$, $X_{35}$, and $X_{36}$ each represent, independently of one another, a hydrogen atom or a substituent.

The term "substituent" as herein employed refers to a halogen atom, a substituted or unsubstituted alkyl group, a substituted or unsubstituted aryl group, or a cyano group.

The halogen atom, the alkyl group, and the aryl group represented by $X_{28}$ to $X_{36}$, and the substituents with which the alkyl group and the aryl group may be substituted are as defined above for the substituents represented by $X_7$ to $X_{13}$ of the above general formula (2).

As the fused heterocyclic group having four or less rings, there is also preferably included a substituent represented by the following general formula (6).

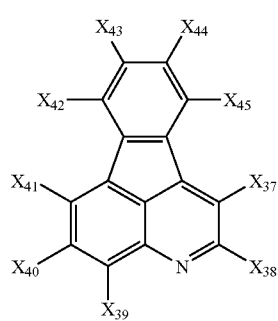

(6)

In the general formula (6), one of $X_{37}$, $X_{38}$, $X_{39}$, $X_{40}$, $X_{41}$, $X_{42}$, $X_{43}$, $X_{44}$, and $X_{45}$ represents a bond, and the others of $X_{37}$, $X_{38}$, $X_{39}$, $X_{40}$, $X_{41}$, $X_{42}$, $X_{43}$, $X_{44}$, and $X_{45}$ each represent, independently of one another, a hydrogen atom or a substituent.

The term "substituent" as herein employed refers to a halogen atom, a substituted or unsubstituted alkyl group, a substituted or unsubstituted aryl group, or a cyano group.

The halogen atom, the alkyl group, and the aryl group represented by $X_{37}$ to $X_{45}$, and the substituents with which the alkyl group and the aryl group may be substituted are as defined above for the substituents represented by $X_7$ to $X_{13}$ of the above general formula (2).

The benzofluoranthene compound of the present invention is preferably used as a material for an organic light-emitting device.

In the benzofluoranthene compound of the present invention, a single fused heterocyclic group with four or less rings having an electron affinity, such as a fused heterocyclic group represented by any one of the general formulae (2) to (6) is incorporated at any position of $X_1$ to $X_6$ represented in the general formula (1). Thereby, the reduction potential of the compound itself becomes high, and the electron acceptability of the compound is increased. This effect is attributable to that the compound has a specific electron conduction level at the naphthalene moiety constituted of carbon atoms at 1- to 6-positions of the benzofluoranthene skeleton. Therefore, by incorporating a single fused heterocyclic group described above to any position of $X_1$ to $X_6$ of the benzofluoranthene compound represented by the general formula (1), an electron conduction level suitable for blue light emission can be attained to improve the electron acceptability. Incidentally, the electron conduction level can be determined by a simulation based on molecular orbital calculation of the benzofluoranthene skeleton. Therefore, by appropriately selecting the position and type of a fused heterocyclic group to be incorporated to any position of $X_1$ to $X_6$ represented by the general formula (1), the driving voltage can be reduced, a high luminance can be maintained for a long period of time, and the energization degradation can also be reduced.

However, when two or more of the fused heterocyclic groups are incorporated, since the electron conduction level is further increased as compared to that in the case where a single fused heterocyclic group is incorporated, the energy gap between the electron conduction level and the hole conduction level becomes smaller. As a result, the emission color shifts to a longer wavelength region, so that the compound is no longer suitable for a blue-light-emitting material.

On the other hand, when a fused heterocyclic group to be incorporated at any position of $X_1$ to $X_6$ of the benzofluoranthene compound represented by the general formula (1) has more than four rings, the molecular weight of the compound is so large that thermal decomposition of the compound may be caused at the time of sublimation to reduce the sublimation property. Further, when a fused heterocyclic ring having more than four rings is incorporated, the emission color will shift to a longer wavelength region, so that the compound is no longer suitable for a blue-light-emitting material having good color purity. Moreover, when a fused heterocyclic group having more than four rings is incorporated, the incorporated fused heterocyclic group rather than the benzofluoranthene skeleton becomes a main light-emitting moiety in the entire molecule of the compound, so that reduction in fluorescent quantum yield may be caused, which is not preferable.

Therefore, by setting the number of fused heterocyclic groups to be incorporated as $X_1$ to $X_6$ represented in the general formula (1) to one and by limiting the fused heterocyclic group to a group having four or less rings, a blue-light-emitting material having a good color purity and high electron acceptability can be provided. The fused heterocyclic group is preferably a fused heterocyclic group having two or more and four or less rings, more preferably a fused heterocyclic group represented by any one of the general formulae (2) to (6).

In addition, in order to provide an organic light-emitting device having an optical output with a high efficiency, it is indispensable to improve the quantum yield of a light-emitting material to be used in the organic light-emitting device. A benzofluoranthene skeleton generally has a fluorescent quantum yield which is higher than that of any other fused polycyclic aromatic ring. However, in order to further improve the fluorescent quantum yield, it is more preferable to incorporate therein a fused heterocyclic group represented by any one of the general formulae (2) to (6) at the position of $X_3$ or $X_4$ represented in the general formula (1). In addition, because the positions of $X_3$ and $X_4$ represented in the general formula (1) are high in reactivity, the incorporation of the fused heterocyclic group represented by any one of the general formulae (2) to (6) at those positions additionally improves the chemical stability of the material.

Further, by appropriately designing not only the position at which the fused heterocyclic group is incorporated but also the type of the fused heterocyclic group and the position at which the compound represented by the general formula (1) and the fused heterocyclic group are bonded to each other, the molecular vibration can be controlled, so that the emission spectrum can be made monodisperse and can also be reduced in full width at half maximum. As a result, blue light having a good color purity can be emitted.

As described above, the incorporation of a single fused heterocyclic ring having four or less rings to 3- or 4-position of a benzofluoranthene skeleton can increase the fluorescent quantum yield of a material for an organic light-emitting device. In addition, the molecular vibration can be controlled, so that the emission spectrum can be made monodisperse and can also be reduced in full width at half maximum. Thereby, a blue-light-emitting material having a high efficiency and good color purity can be provided.

Hereinafter, specific structural formulae for the benzofluoranthene compound of the present invention are shown below. However, those formulae are merely representative examples, and the present invention is not limited to the examples.

Compound Example 1

Compound examples in each of which $X_3$ or $X_4$ in the general formula (1) is represented by the general formula (2), and $X_7$ in the general formula (2) represents a bond.

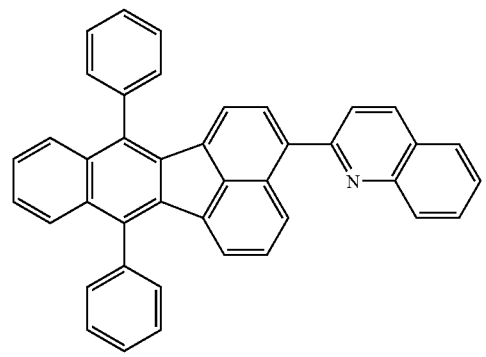

101

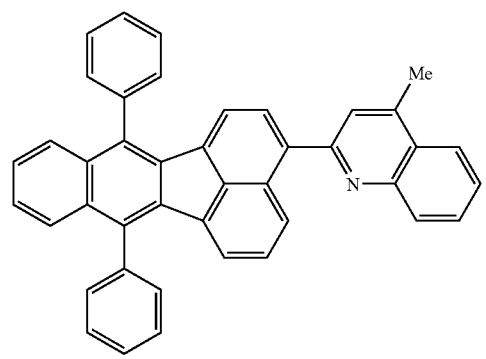

102

103
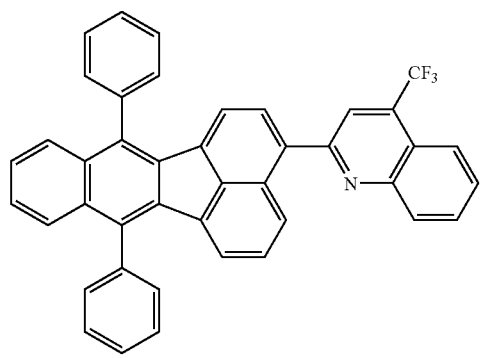
104
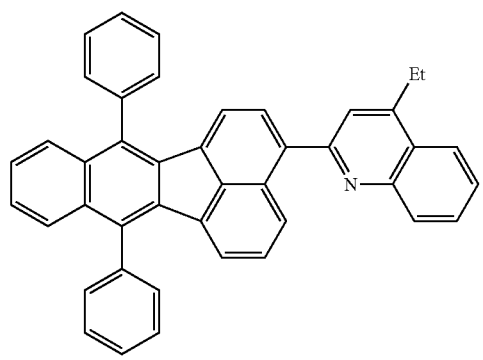
105
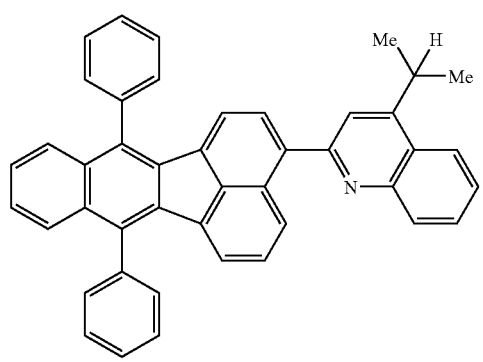
106
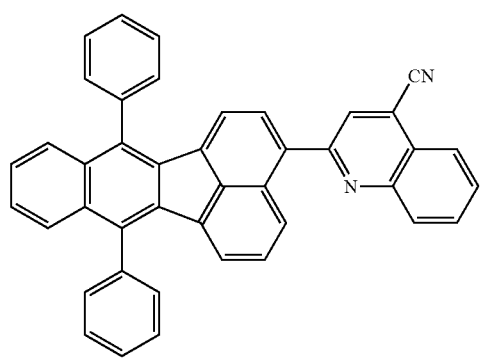
107
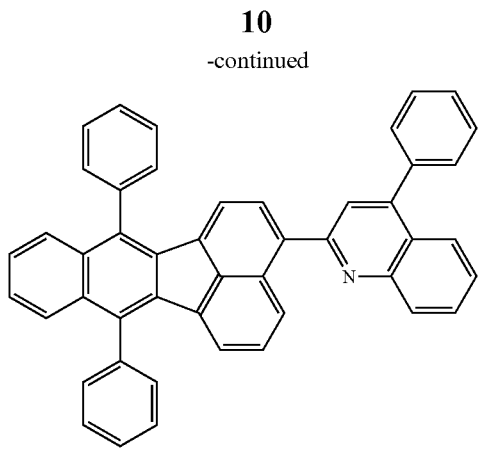
108
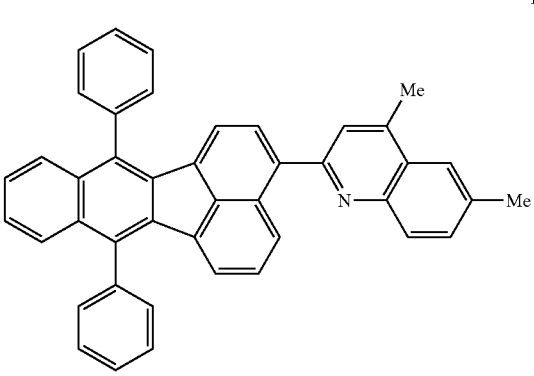
109
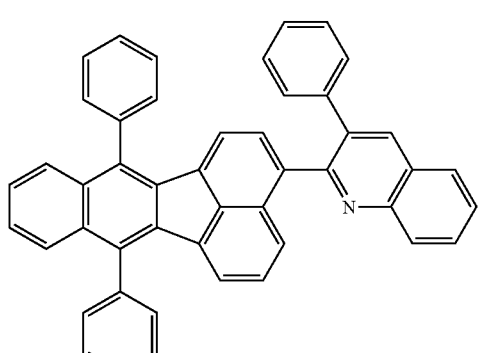
110
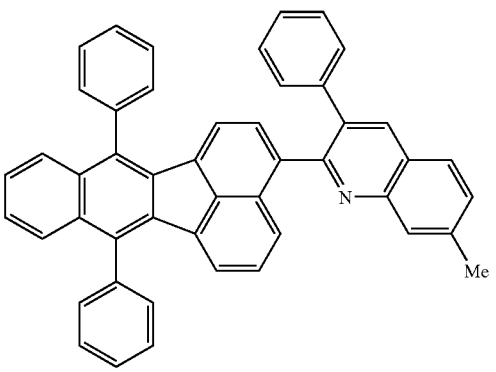

111
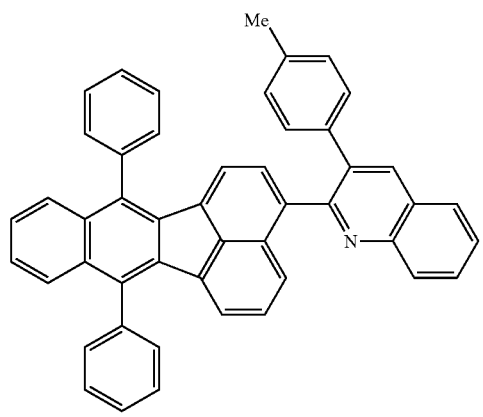
112
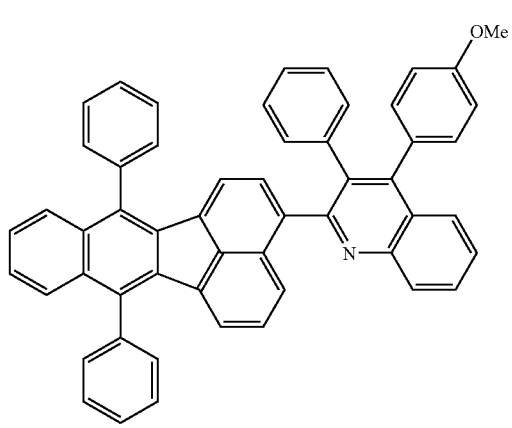
113
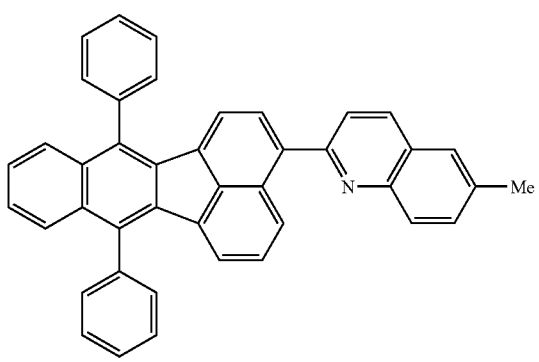
114
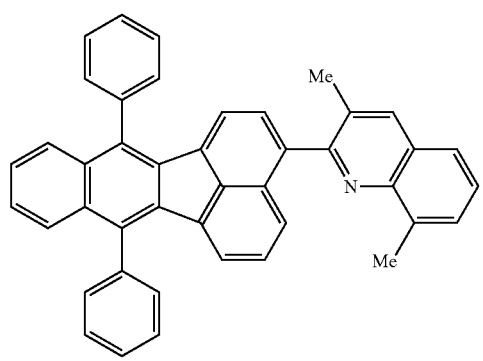
115
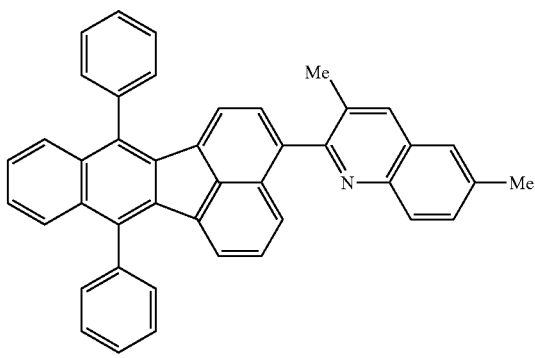
116
117
118
Compound Example 2
Compound examples in each of which $X_3$ or $X_4$ in the general formula (1) is represented by the general formula (2), and $X_8$, $X_{11}$, or $X_{12}$ in the general formula (2) represents a bond.

-continued
119
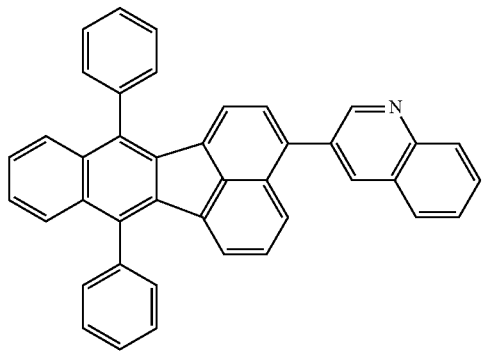
120
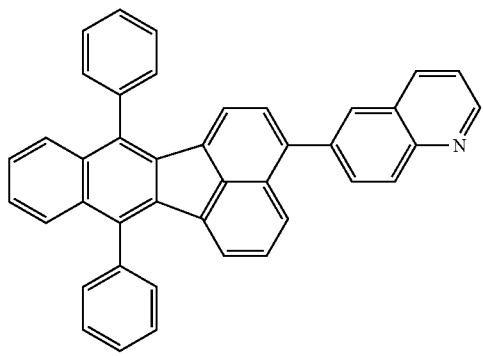
121
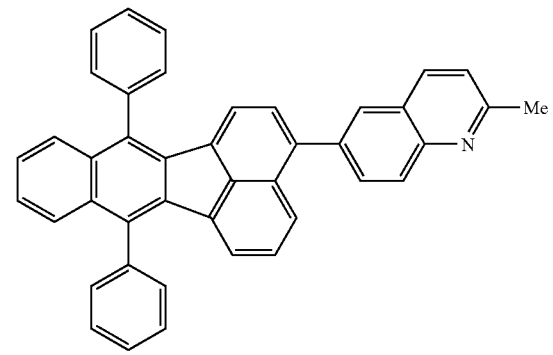
122
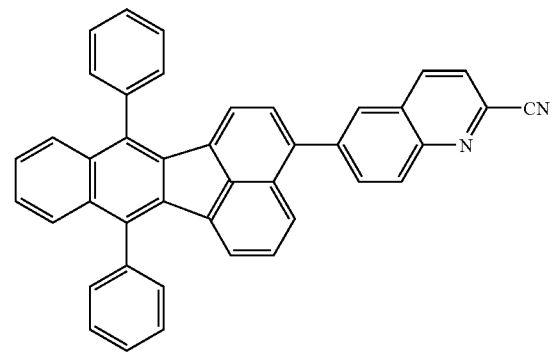
123
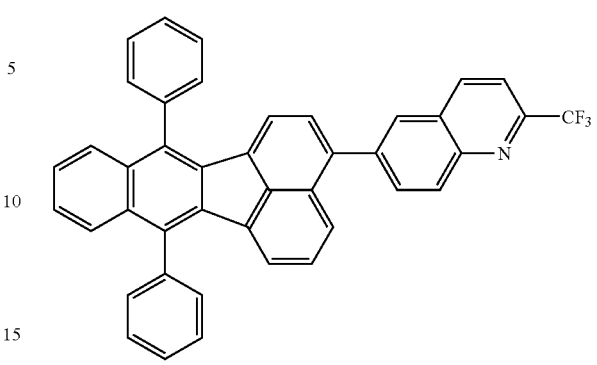
124
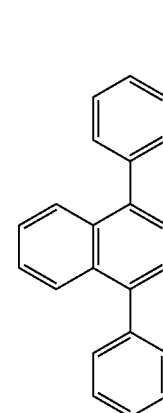
125
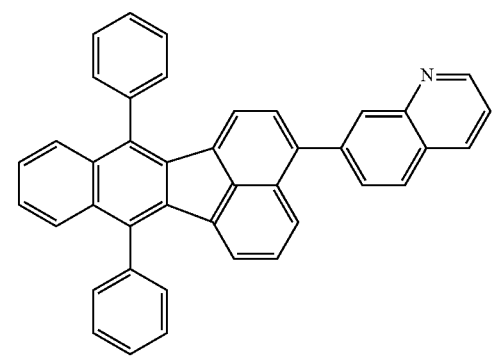
126
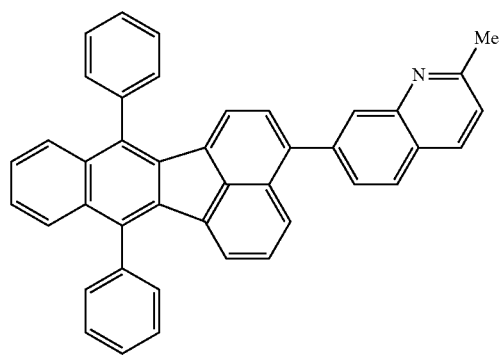

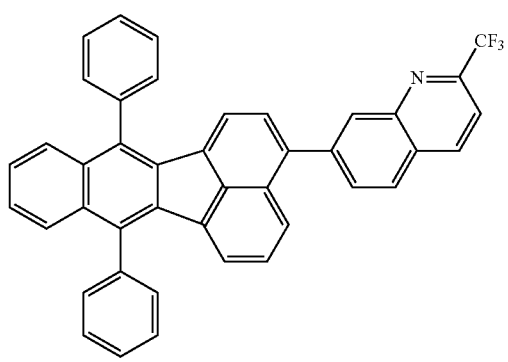
126
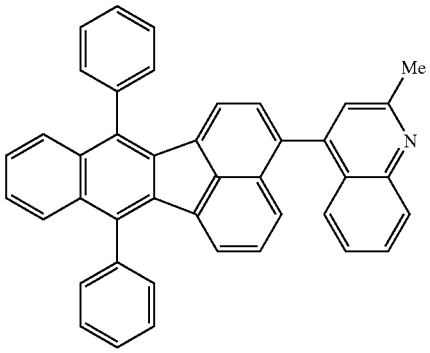
130
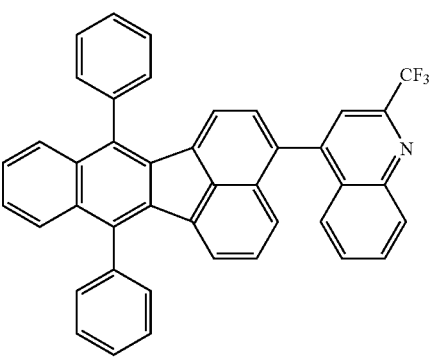
131
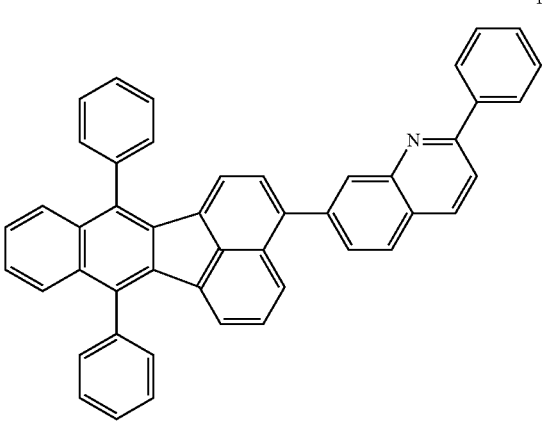
127
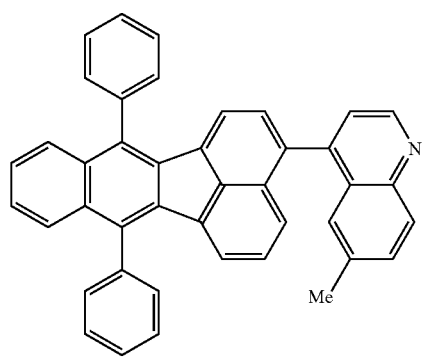
132
Compound Example 3
Compound examples in each of which $X_3$ or $X_4$ in the general formula (1) is represented by the general formula (2), and $X_9$, $X_{10}$, or $X_{13}$ in the general formula (2) represents a bond.
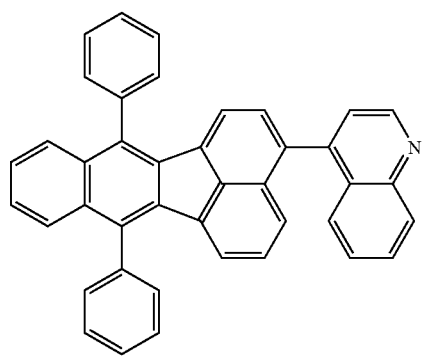
129
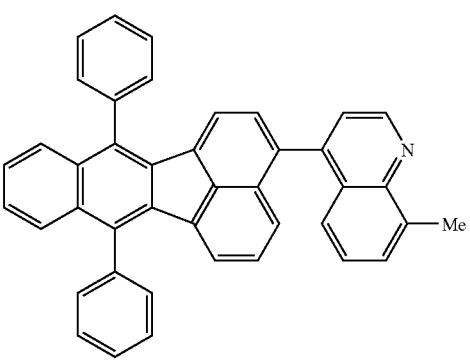
133

134 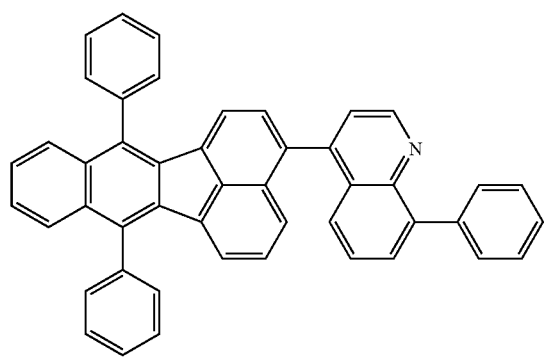
138 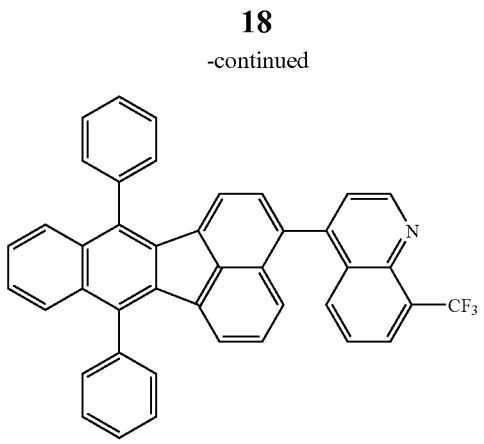
135 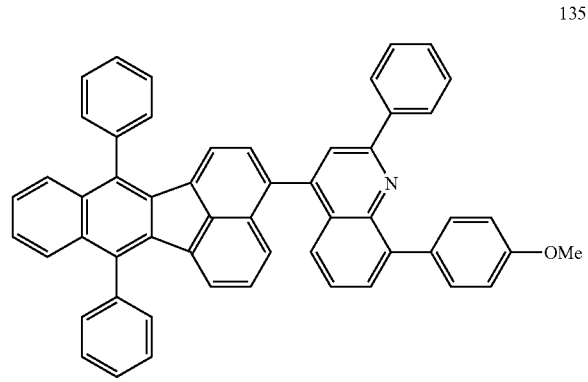
139 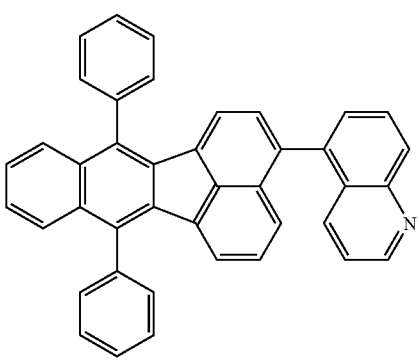
136 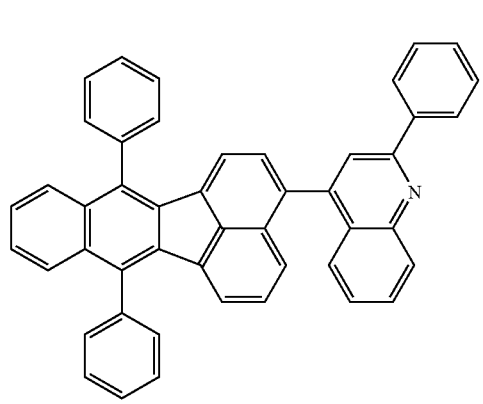
140 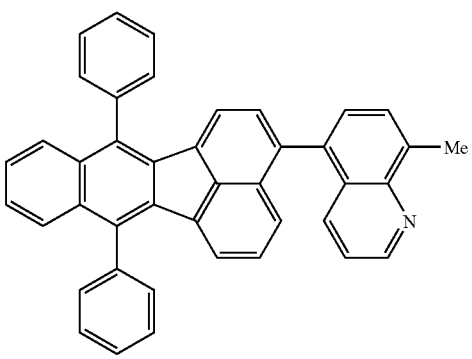
137 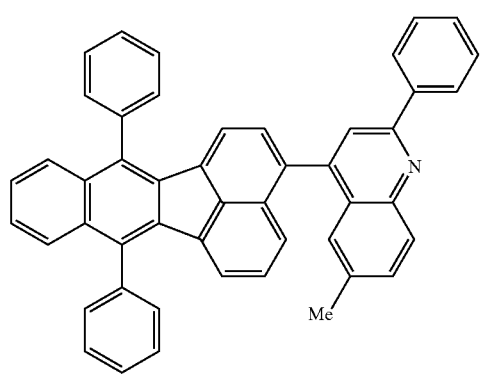
141 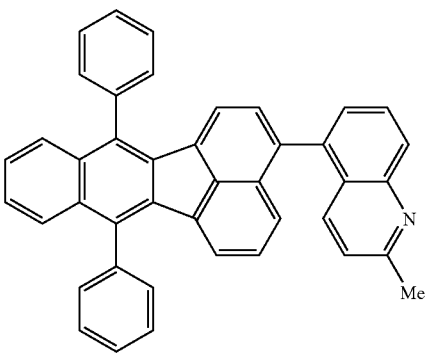

142
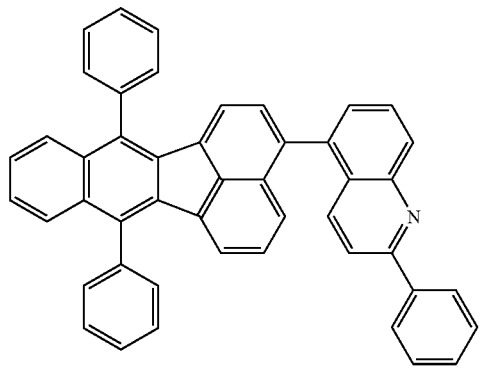
143
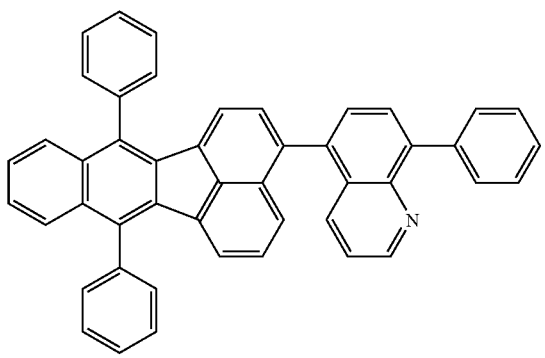
144
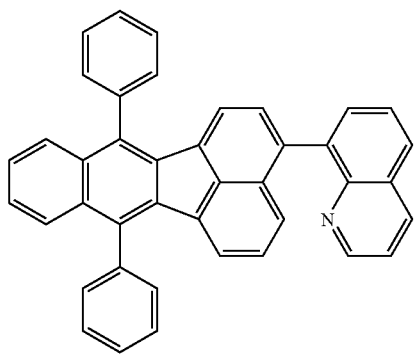
145
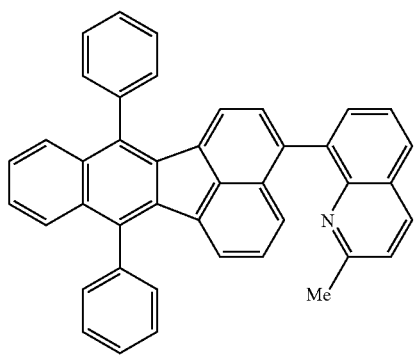
146
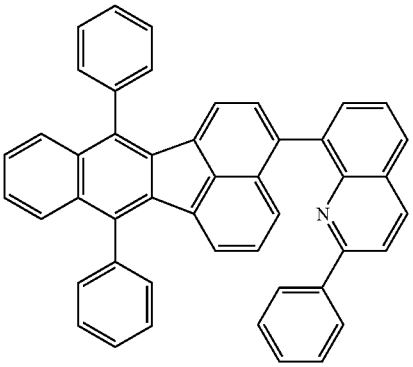
Compound Example 4
Compound examples in each of which $X_3$ or $X_4$ in the general formula (1) is represented by the general formula (3), and $X_{14}$, $X_{16}$, $X_{17}$, or $X_{20}$ in the general formula (3) represents a bond.
201
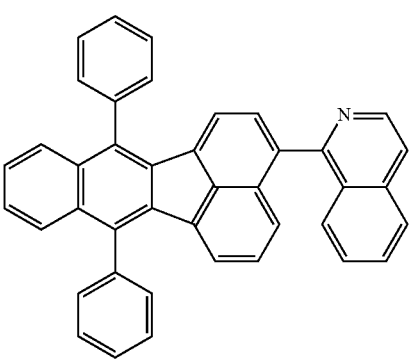
202
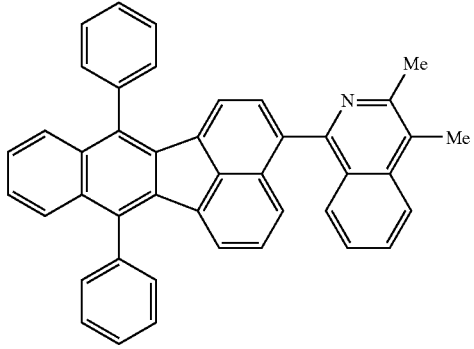
203
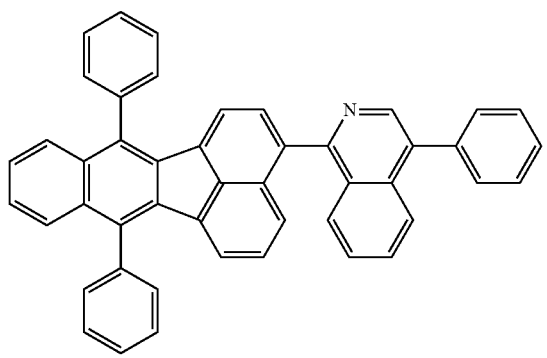

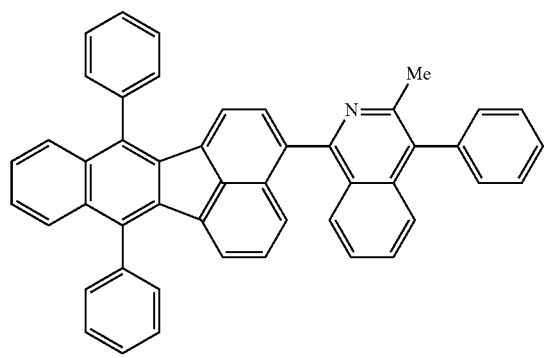
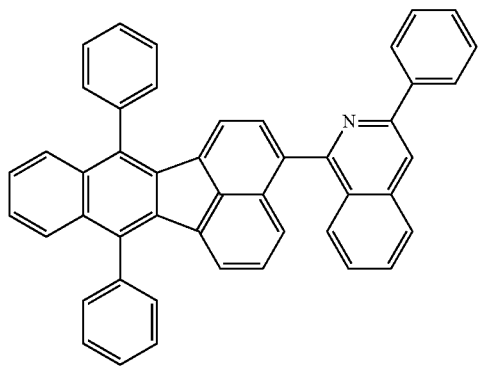
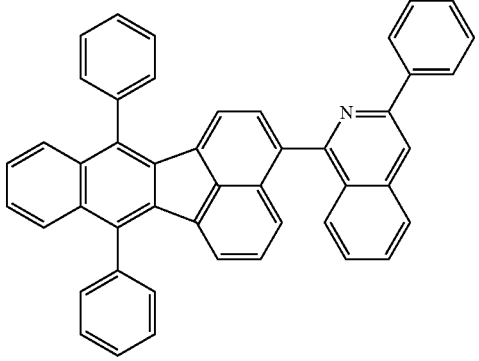
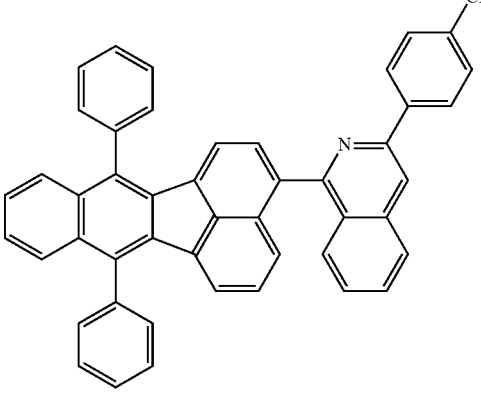
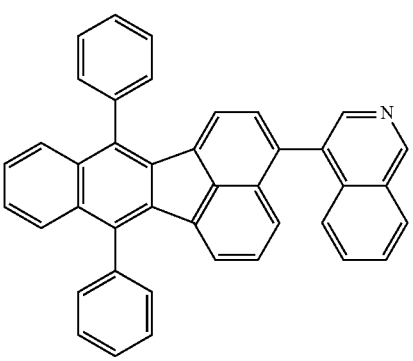

212
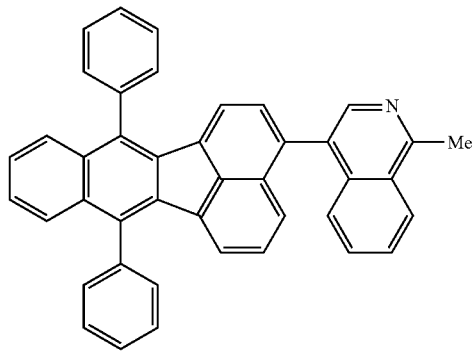
213
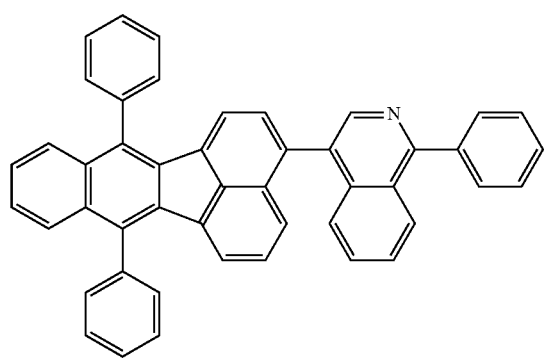
214
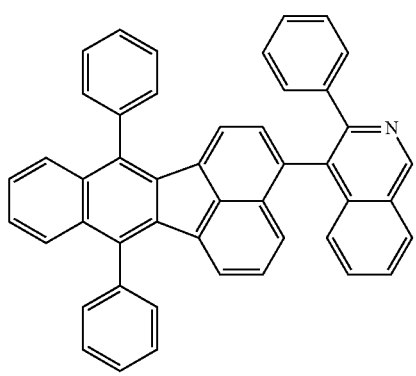
215
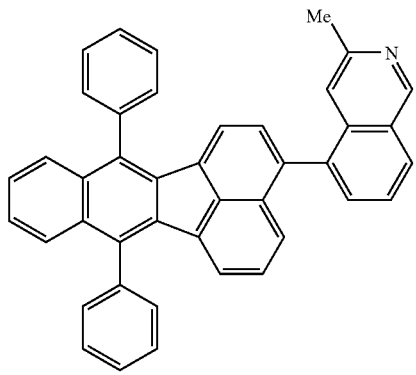
216
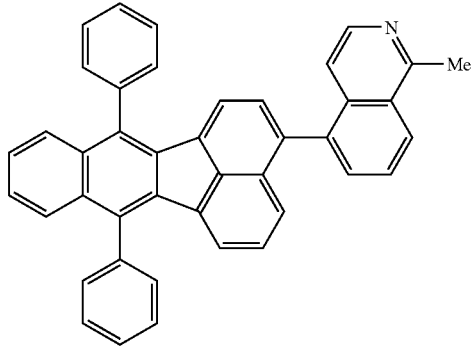
217
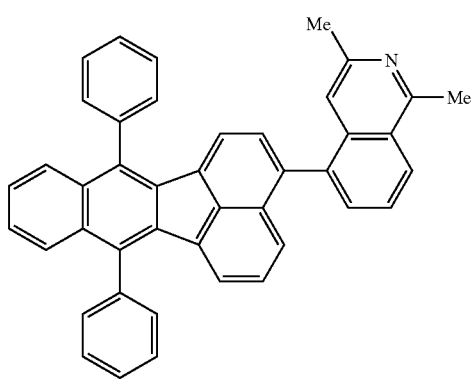
218
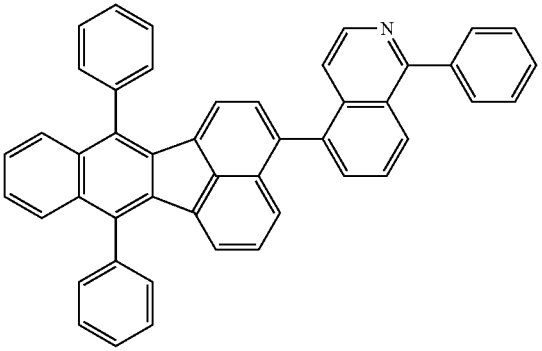
219

220
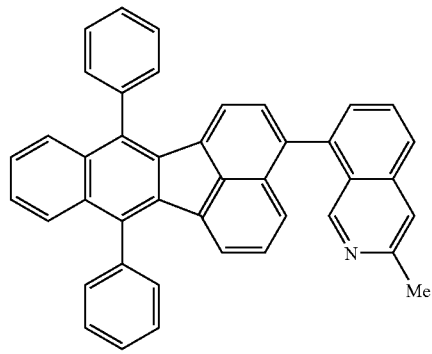
Compound Example 5
Compound examples in each of which $X_3$ or $X_4$ in the general formula (1) is represented by the general formula (3), and $X_{15}$, $X_{18}$, or $X_{19}$ in the general formula (3) represents a bond.
221
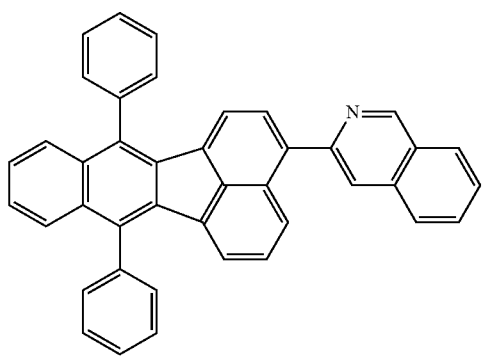
222
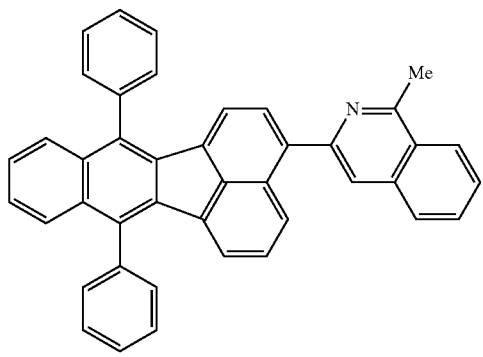
223
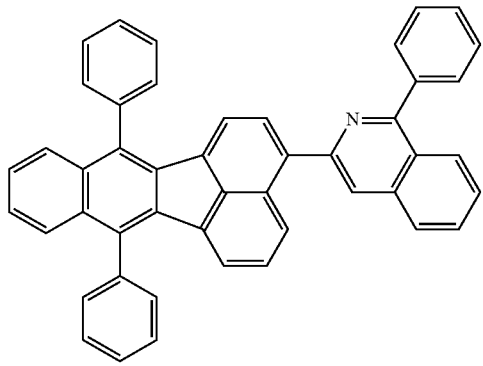
224
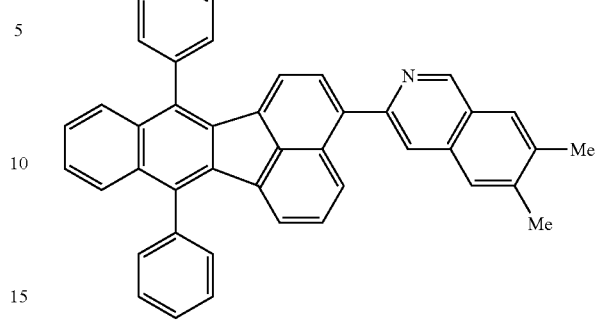
225
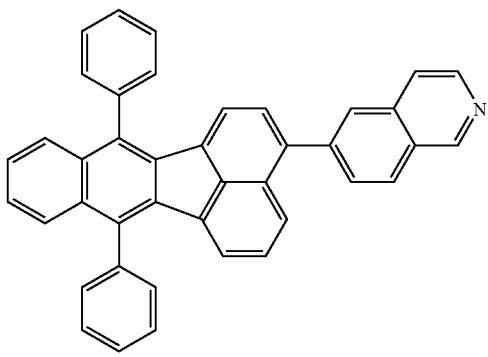
226
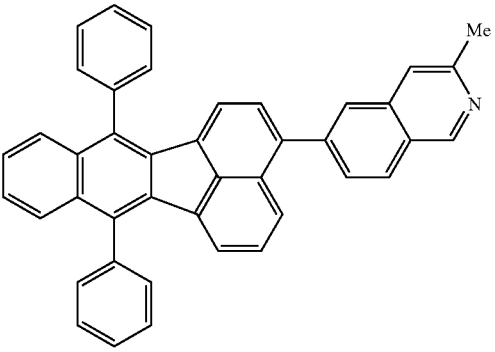
227
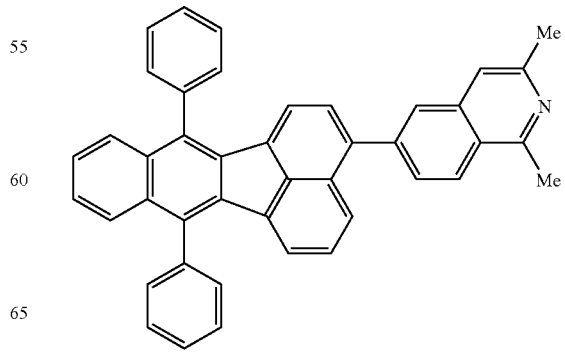

228
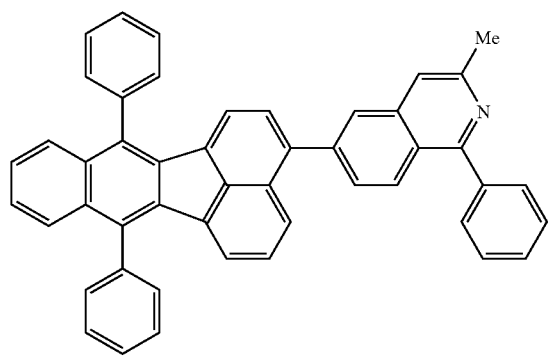
229
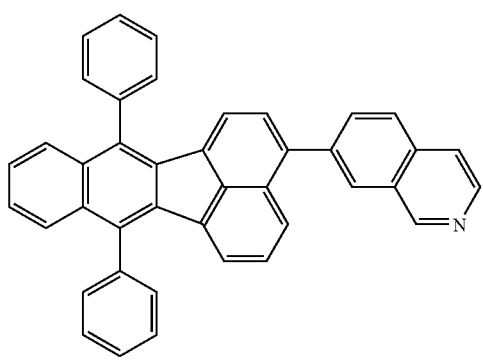
230
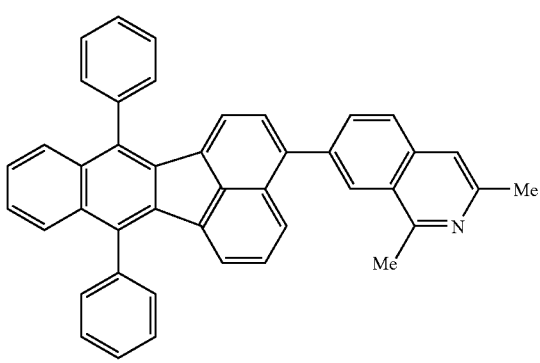
Compound Example 6
Compound examples in each of which $X_3$ or $X_4$ in the general formula (1) is represented by the general formula (4), and $X_{23}$ in the general formula (4) represents a bond.
301
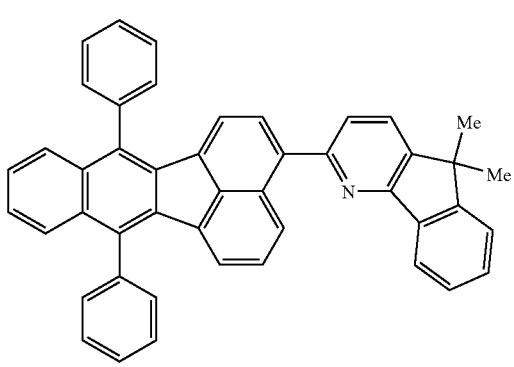
302
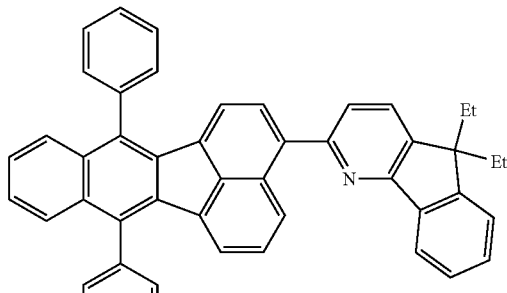
303
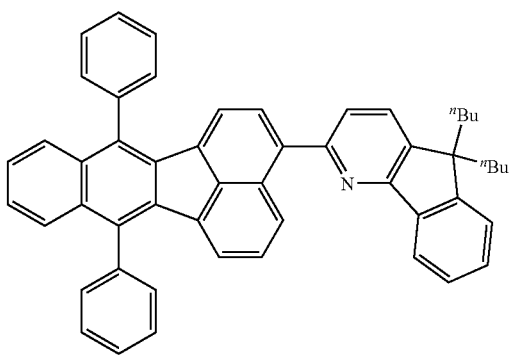
304
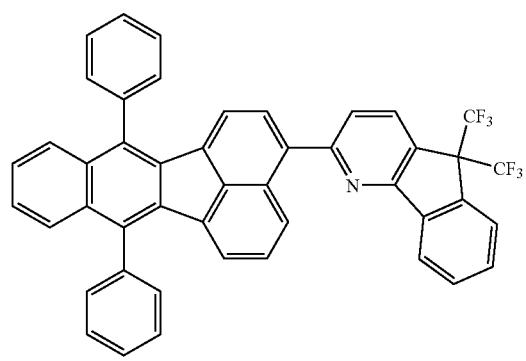
Compound Example 7
Compound examples in each of which $X_3$ or $X_4$ in the general formula (1) is represented by the general formula (4), and $X_{21}$ in the general formula (4) represents a bond.
305
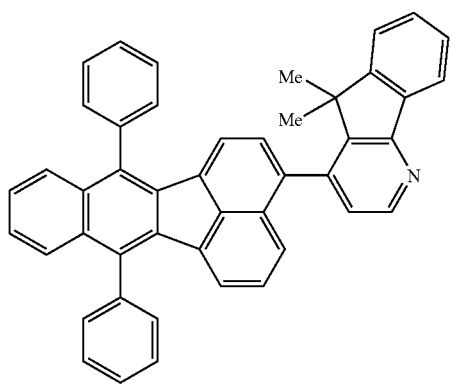

306 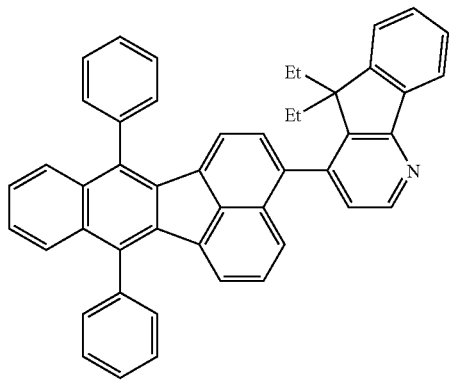
307 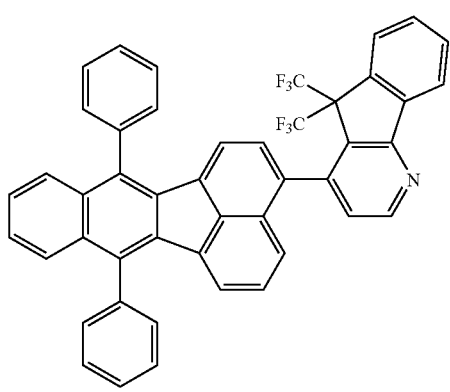
308 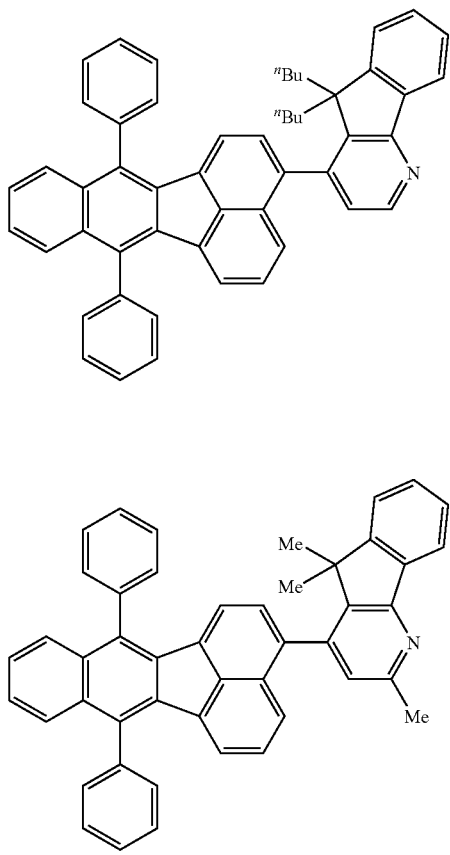
309
310 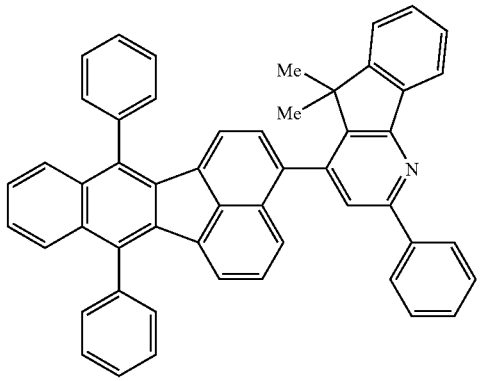
Compound Example 8
Compound examples in each of which $X_3$ or $X_4$ in the general formula (1) is represented by the general formula (4), and $X_{26}$ in the general formula (4) represents a bond.
311 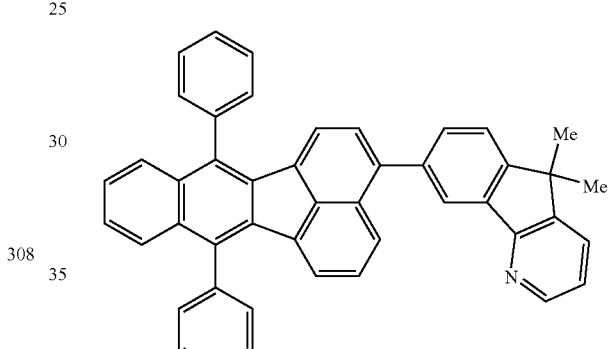
312
313 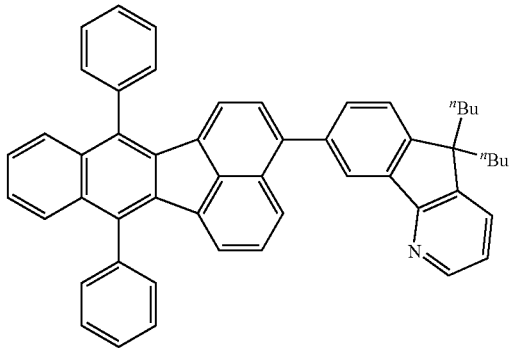

-continued

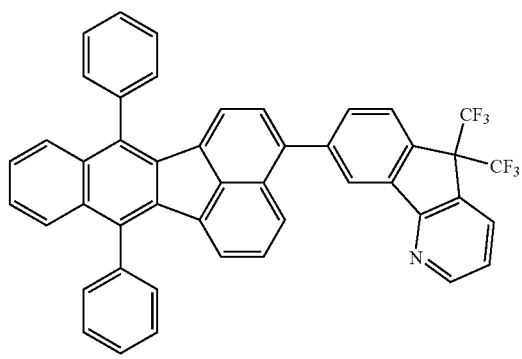
314

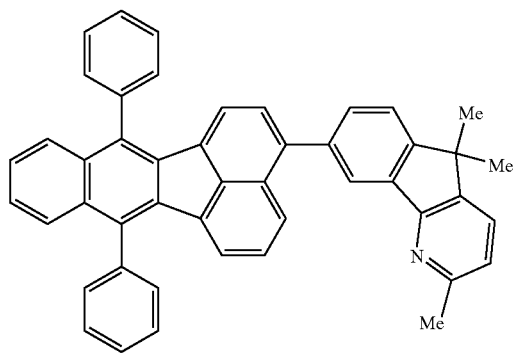
315

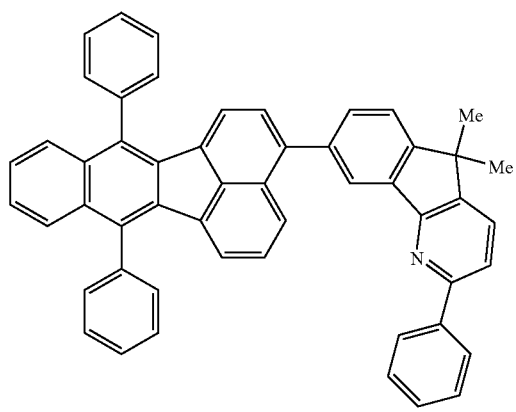
316

Compound Example 9

Compound examples in each of which $X_3$ or $X_4$ in the general formula (1) is represented by the general formula (4), and $X_{25}$ in the general formula (4) represents a bond.

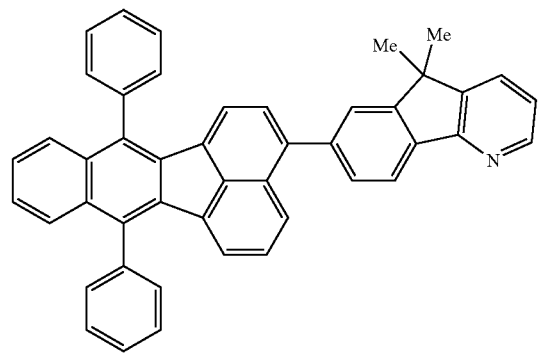
317

-continued

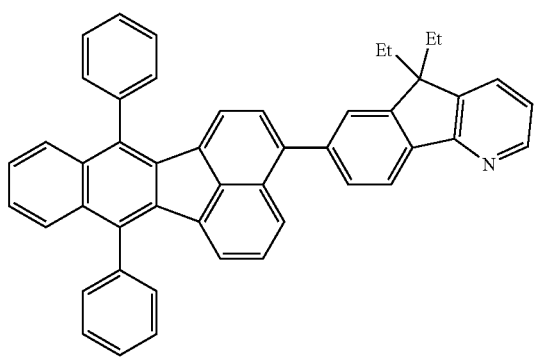
318

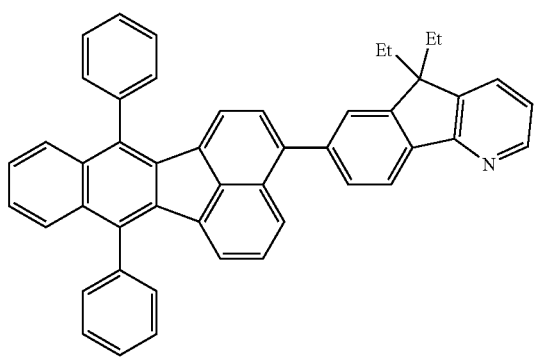
319

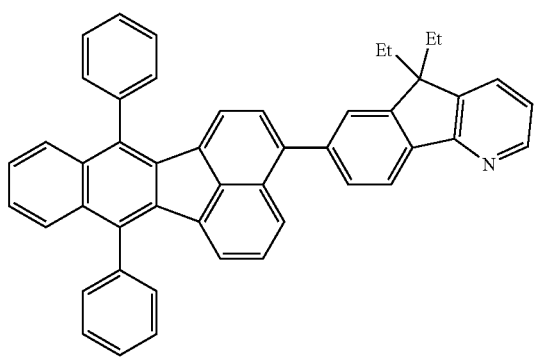
320

Compound Example 10

Compound examples in each of which $X_3$ or $X_4$ in the general formula (1) is represented by the general formula (5), and $X_{36}$ in the general formula (5) represents a bond.

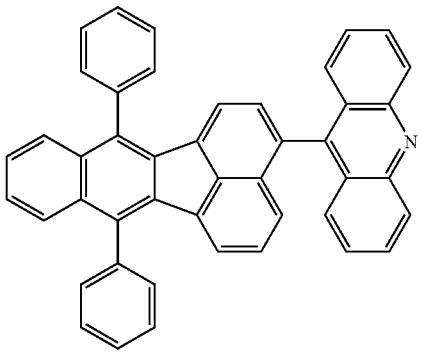
401

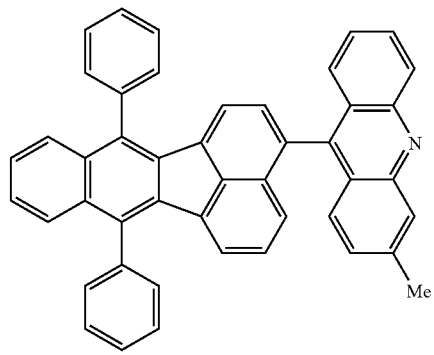
402
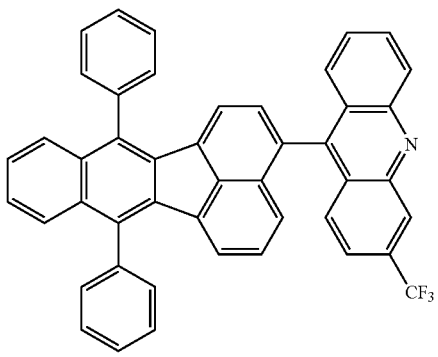
403
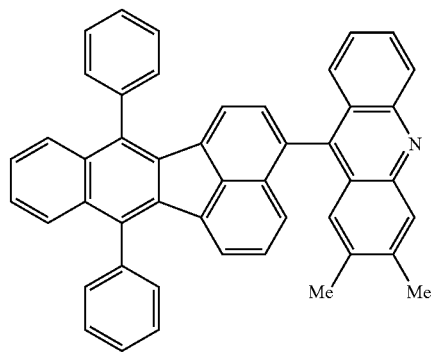
404
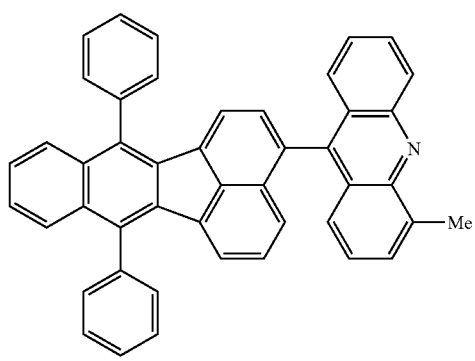
405
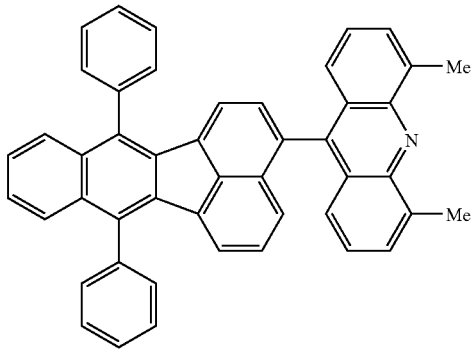
406
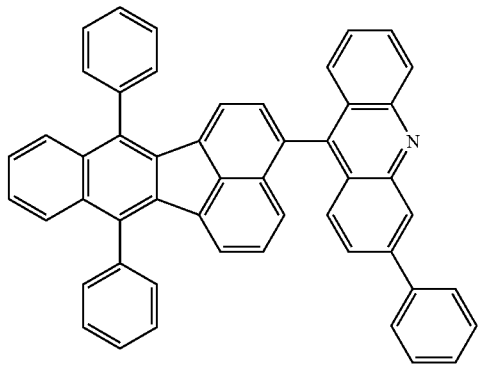
407
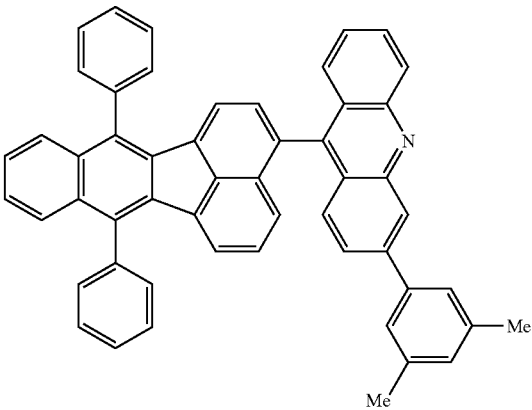
408
Compound Example 11
Compound examples in each of which $X_3$ or $X_4$ in the general formula (1) is represented by the general formula (6), and $X_{38}$ in the general formula (6) represents a bond.
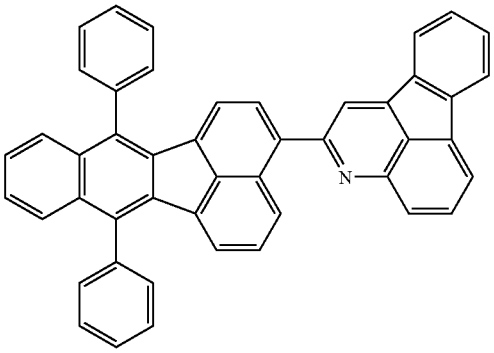
501

-continued
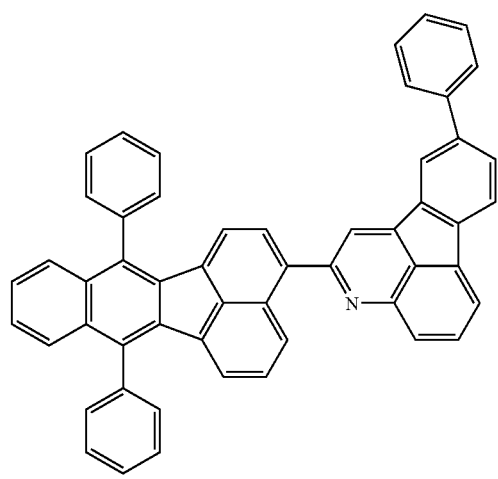 502
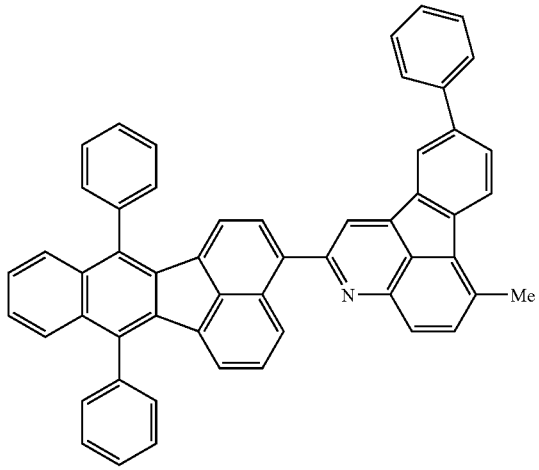 503
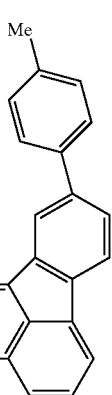 504
-continued
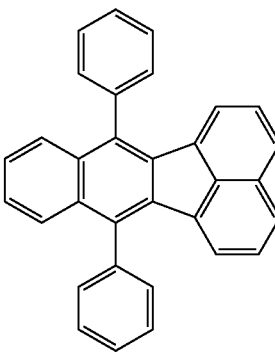 505
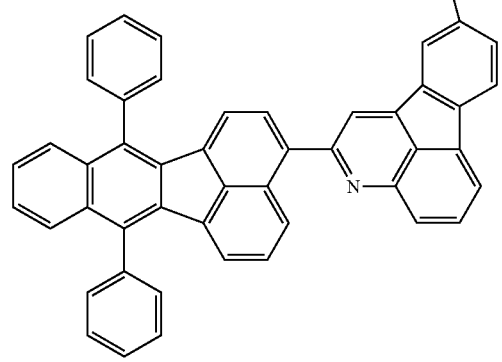 506
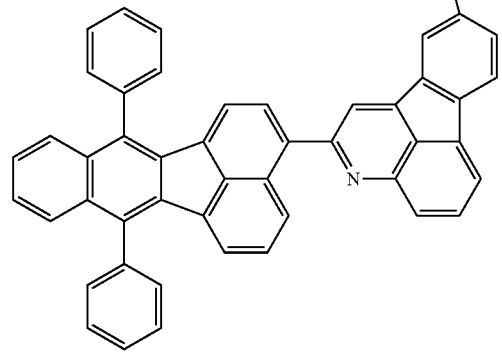 507

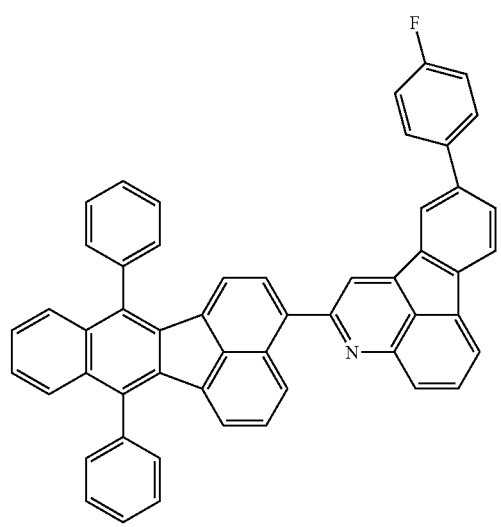
Compound Example 12
Compound examples in each of which $X_3$ or $X_4$ in the general formula (1) is represented by the general formula (6), and $X_{39}$ in the general formula (6) represents a bond.
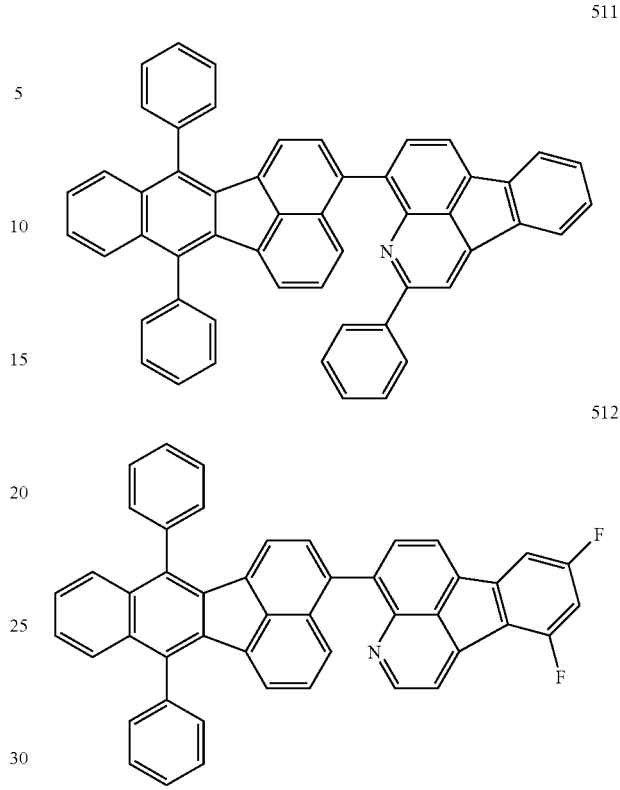
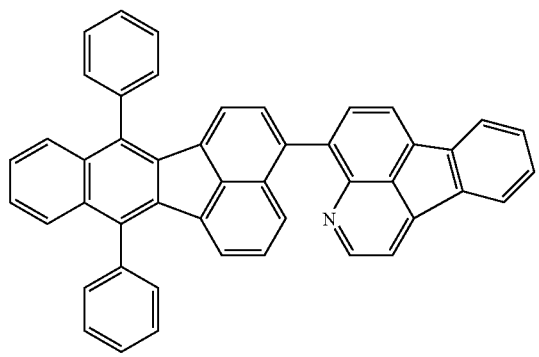
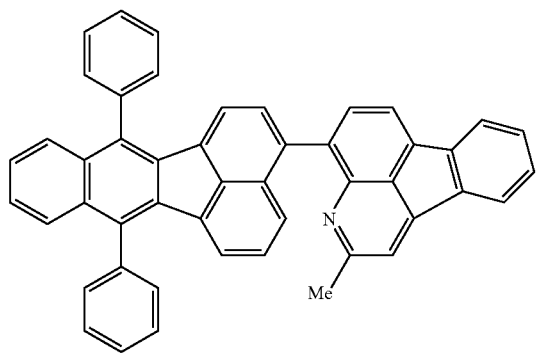
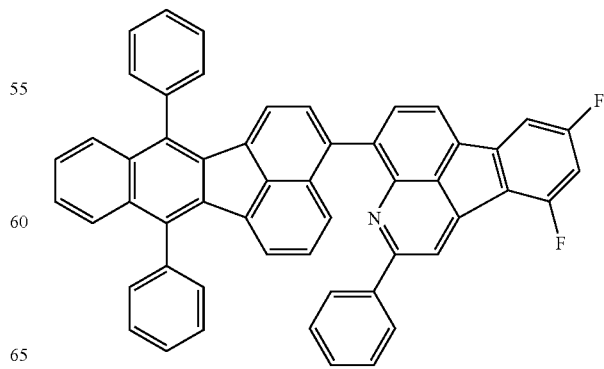

Compound Example 13
Compound examples in each of which $X_3$ or $X_4$ in the general formula (1) is represented by the general formula (6), and $X_{37}$, $X_{40}$, or $X_{41}$ in the general formula (6) represents a bond.
515
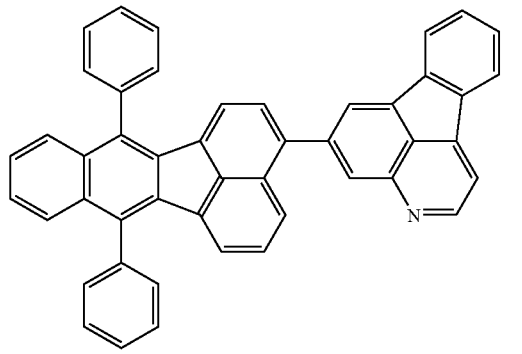
516
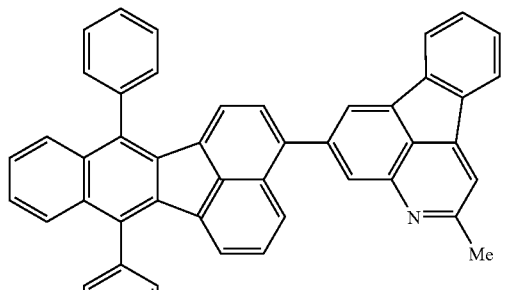
517
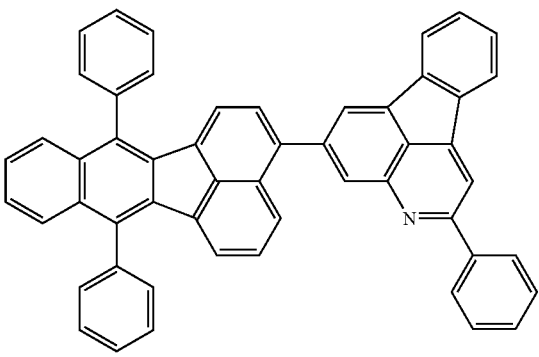
518
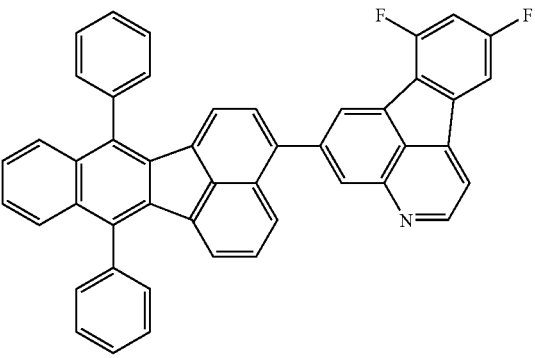
519
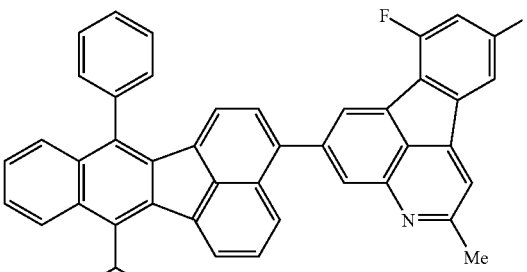
520
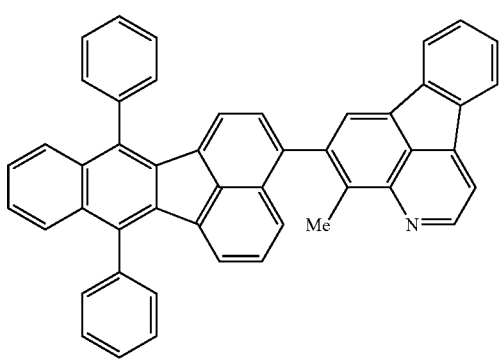
521
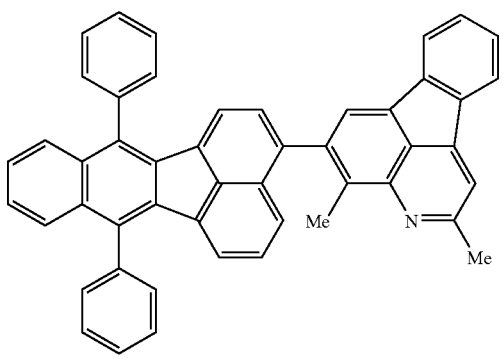
522
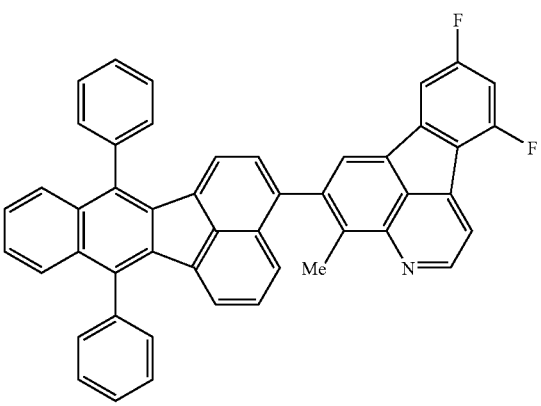

-continued
523
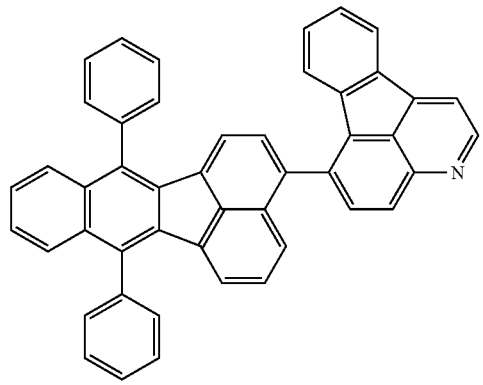
524
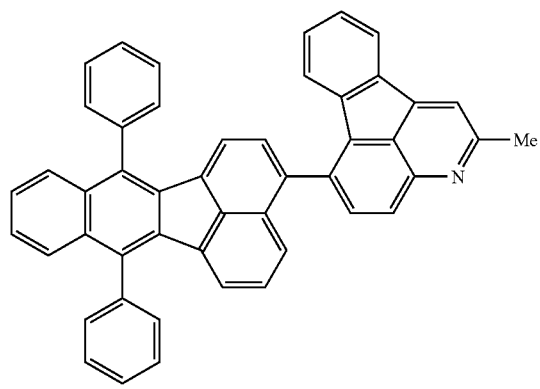
525
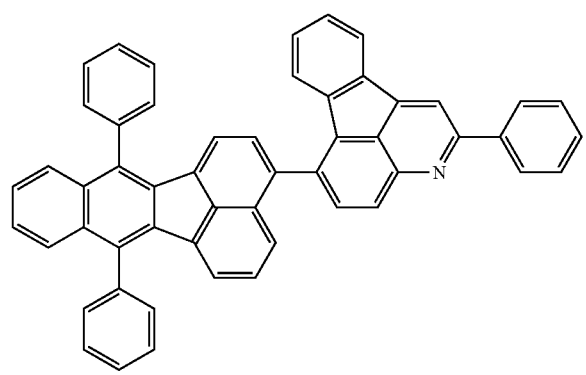
526
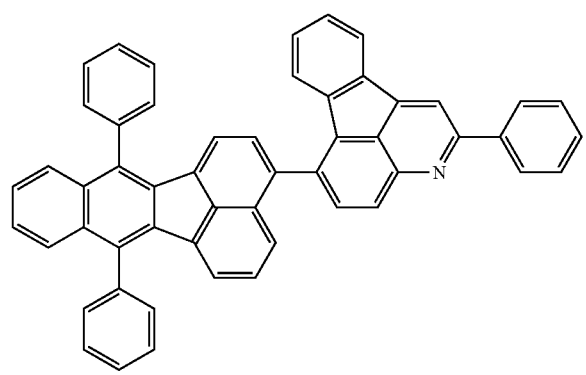
527
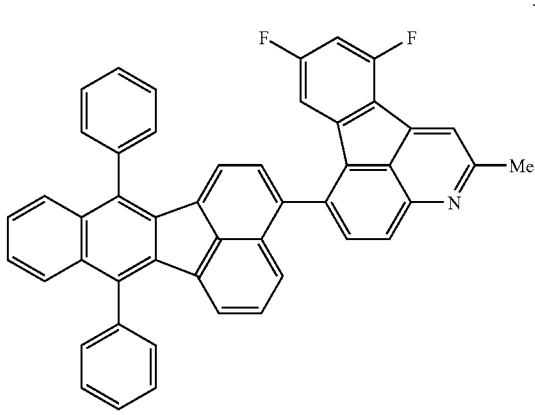
528
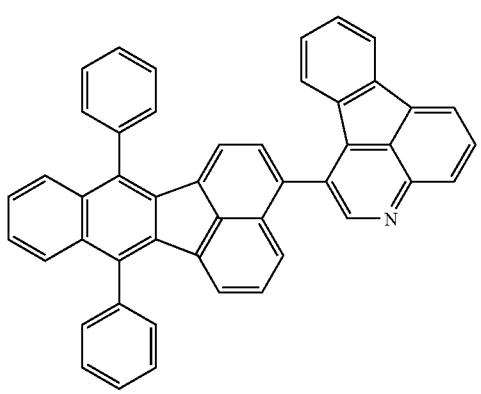
529
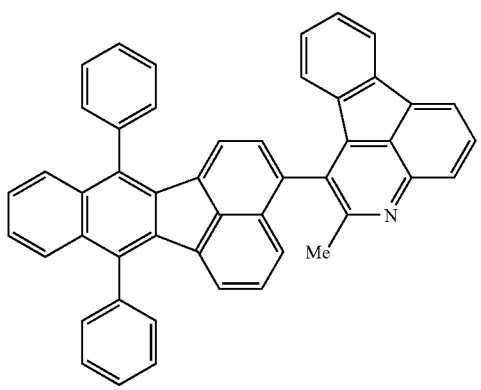
530
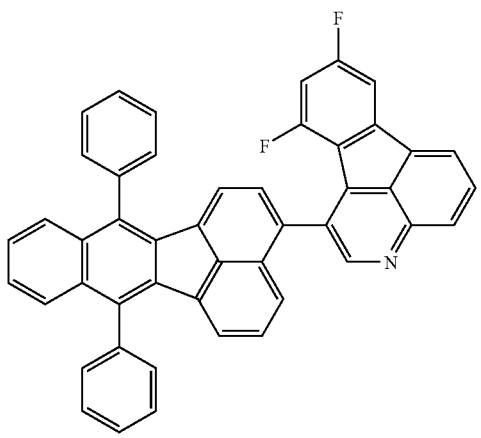

Compound Example 14
Compound examples in each of which $X_3$ or $X_4$ in the general formula (1) is represented by the general formula (6), and any one of $X_{42}$, $X_{43}$, $X_{44}$, and $X_{45}$ in the general formula (6) represents a bond.
531
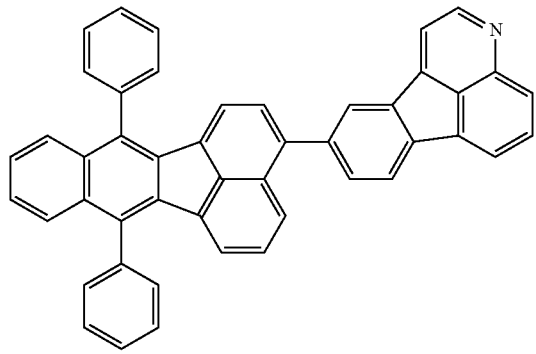
532
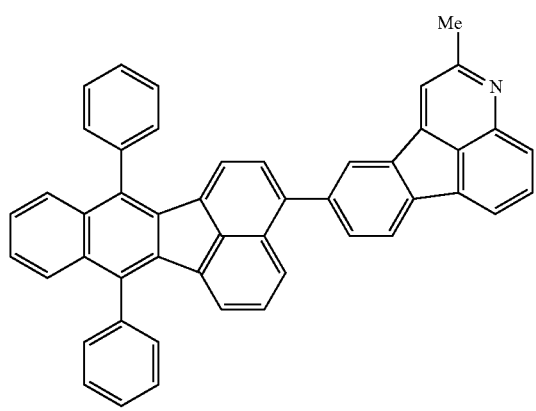
533
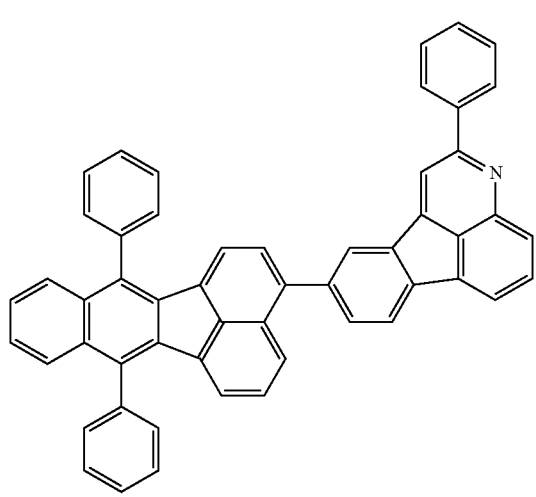
534
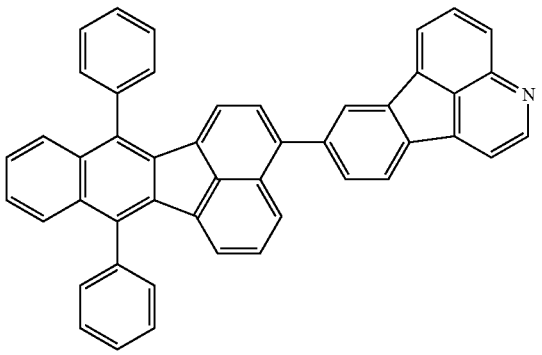
535
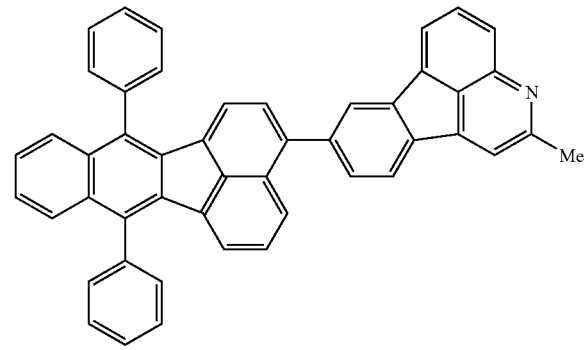
536
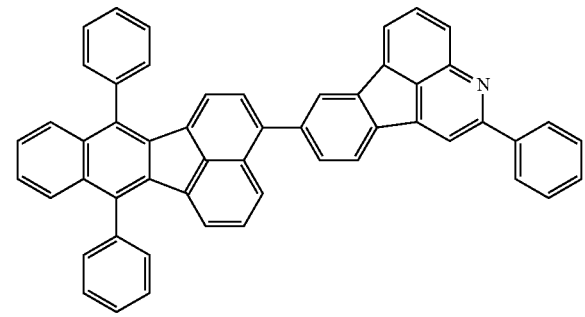
537
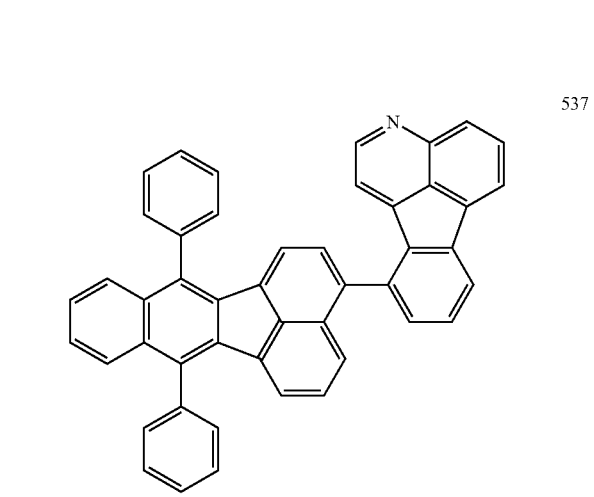

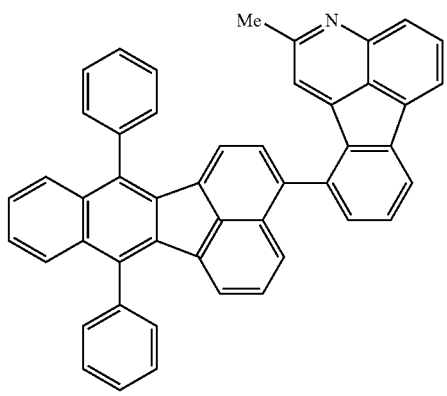
538
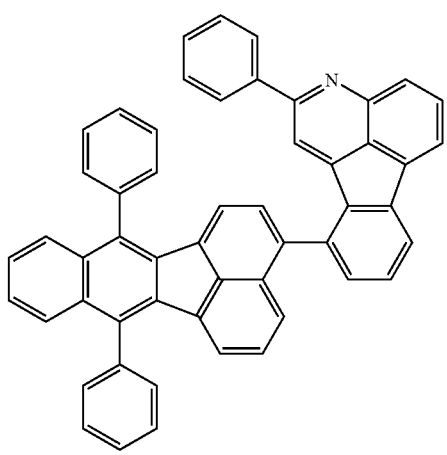
539
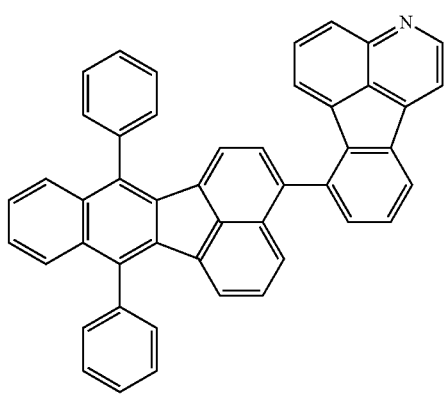
540
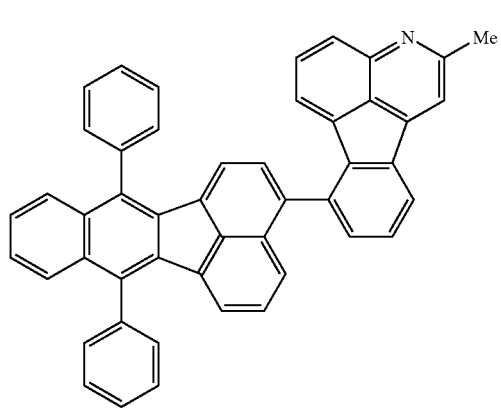
541
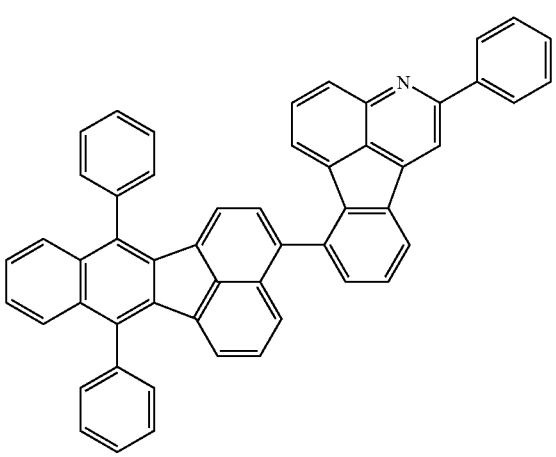
542
Compound Example 15
Compound examples in each of which $X_3$ or $X_4$ in the general formula (1) is represented by the general formula (1), and the fused heterocyclic ring in the general formula (1) contains two or more hetero atoms.
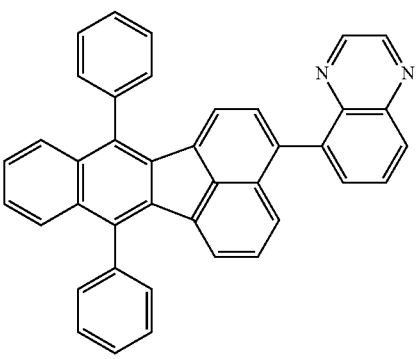
601
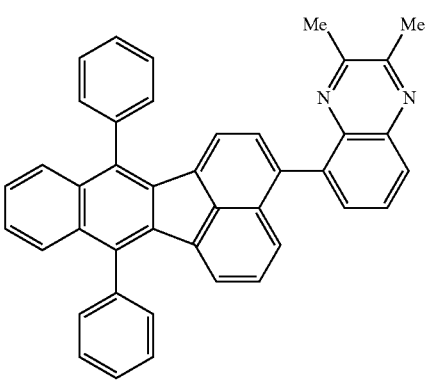
602

603
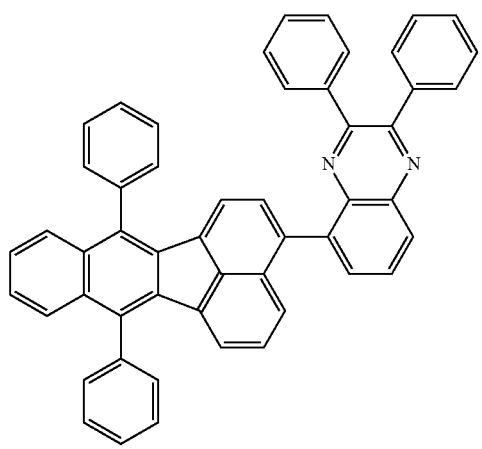
604
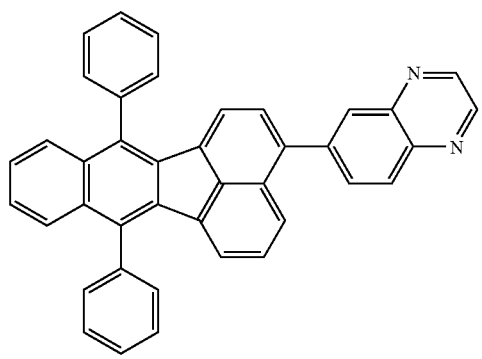
605
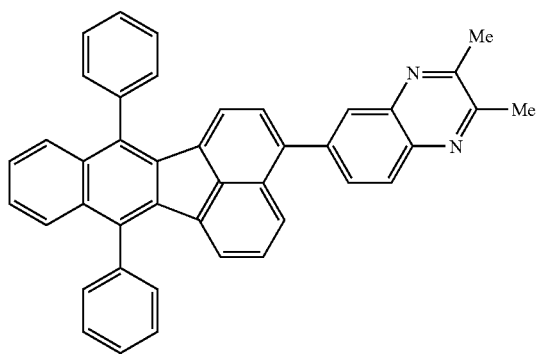
606
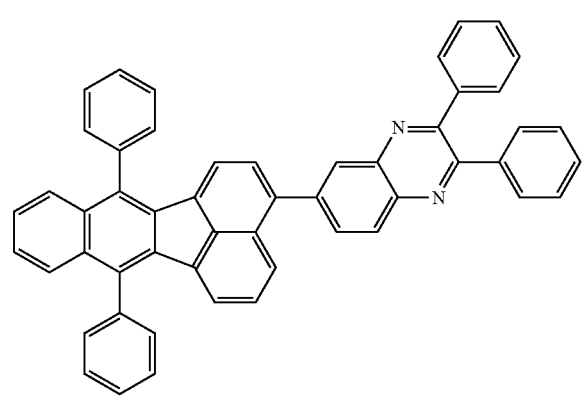
607
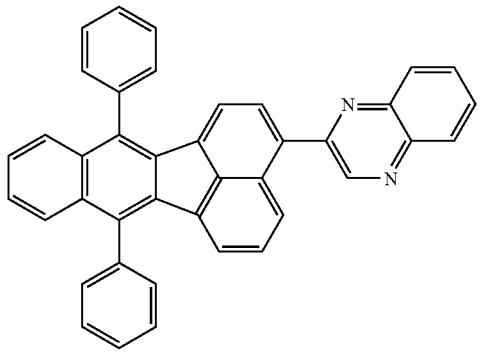
608
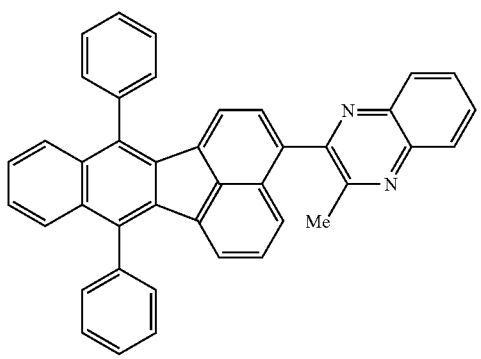
609
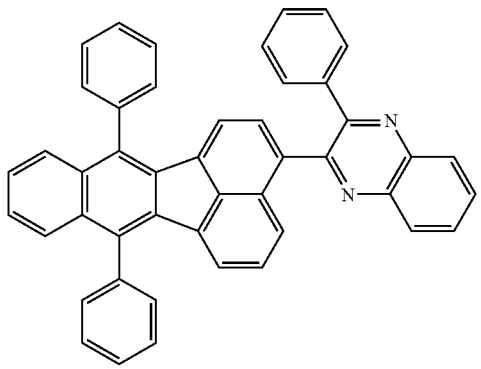
610
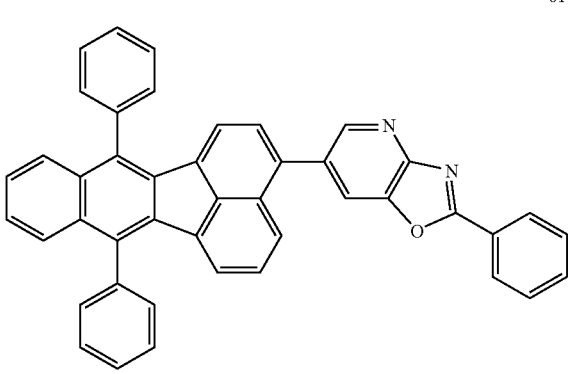

-continued
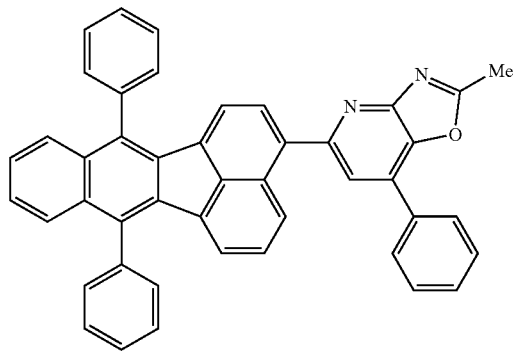
611
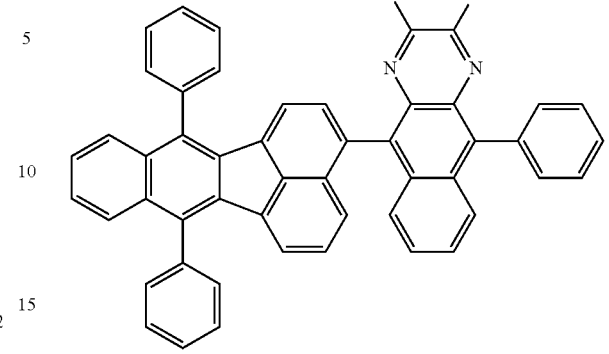
615
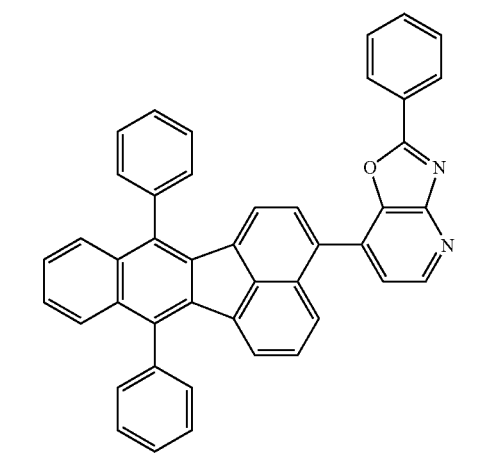
612
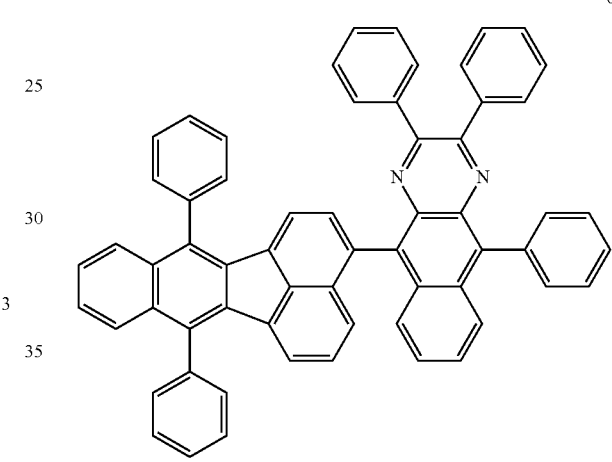
616
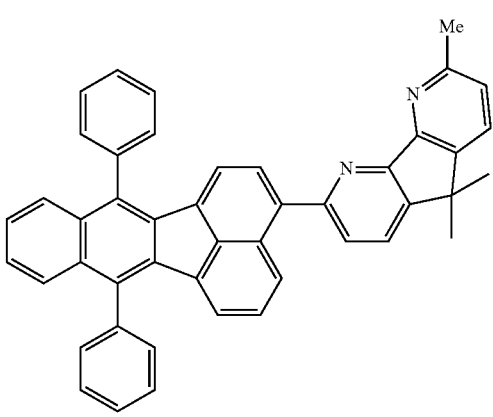
613
Compound Example 16
Compound examples in each of which $X_2$ or $X_5$ in the general formula (1) is represented by the general formula (2), and $X_7$, $X_8$, $X_{11}$, or $X_{12}$ in the general formula (2) represents a bond.
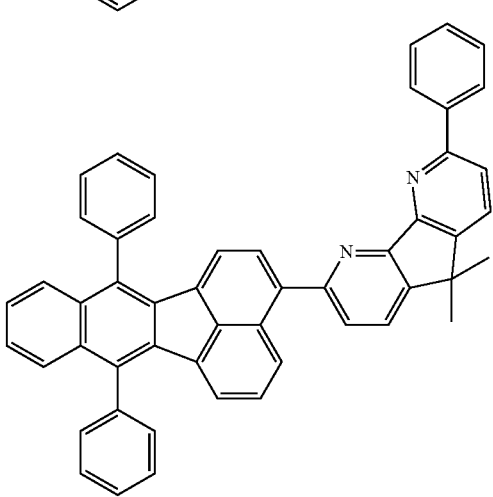
614
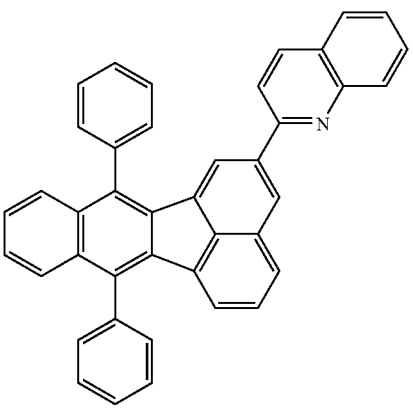
701

-continued
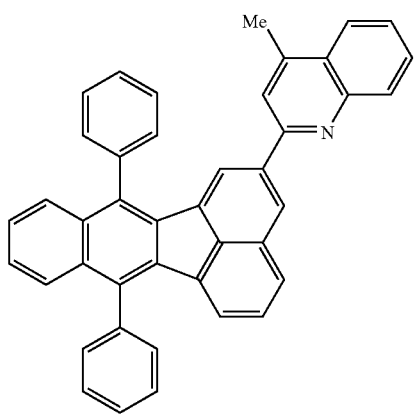
702
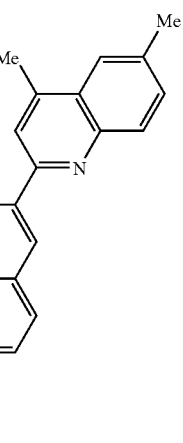
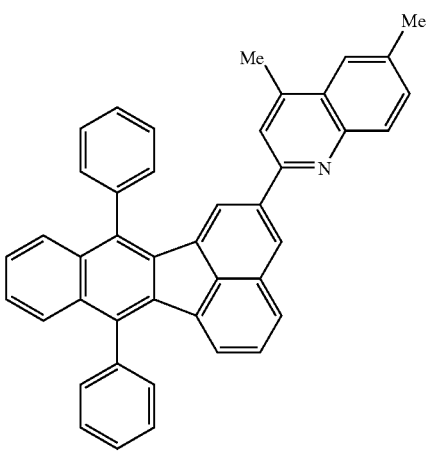
705
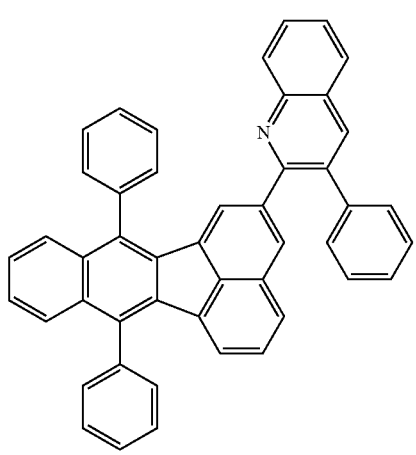
703
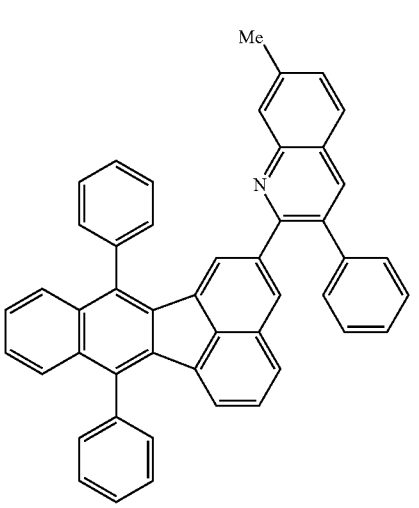
706
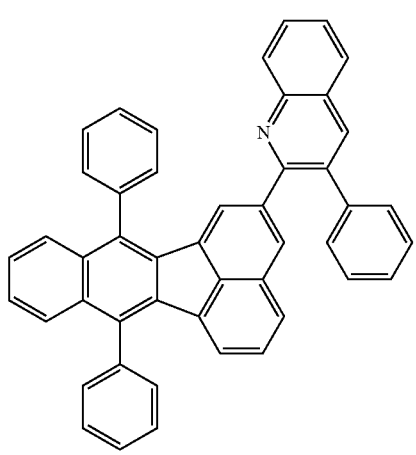
704
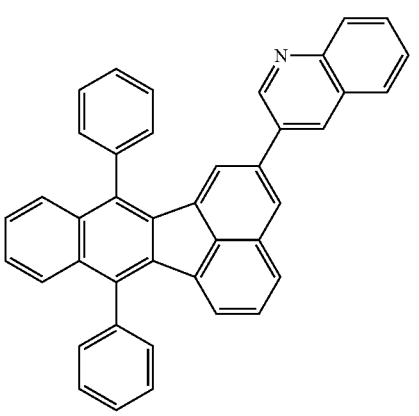
707

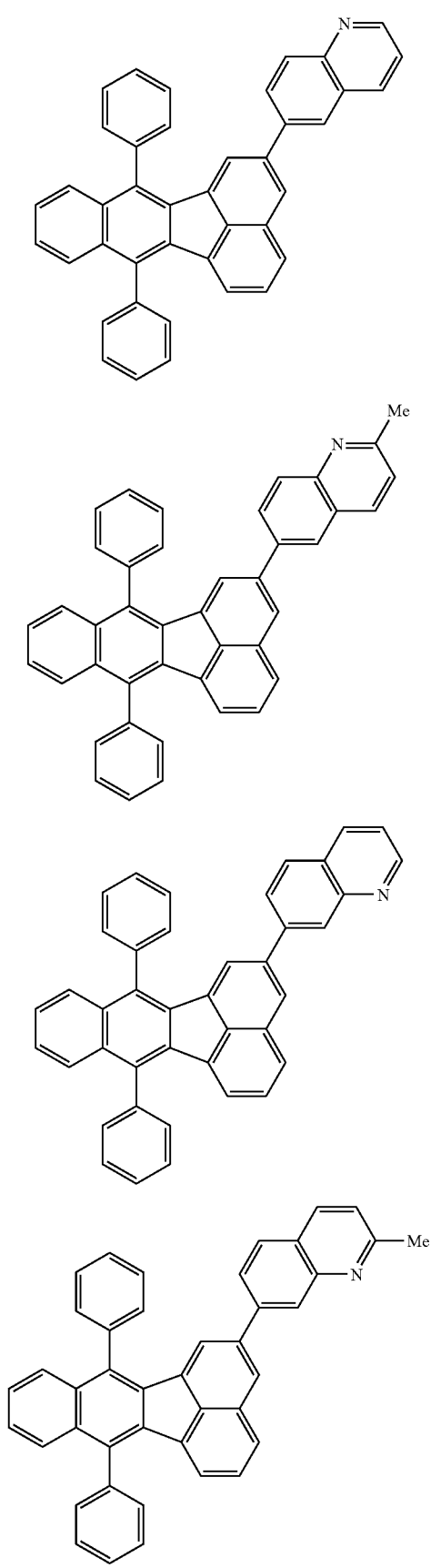
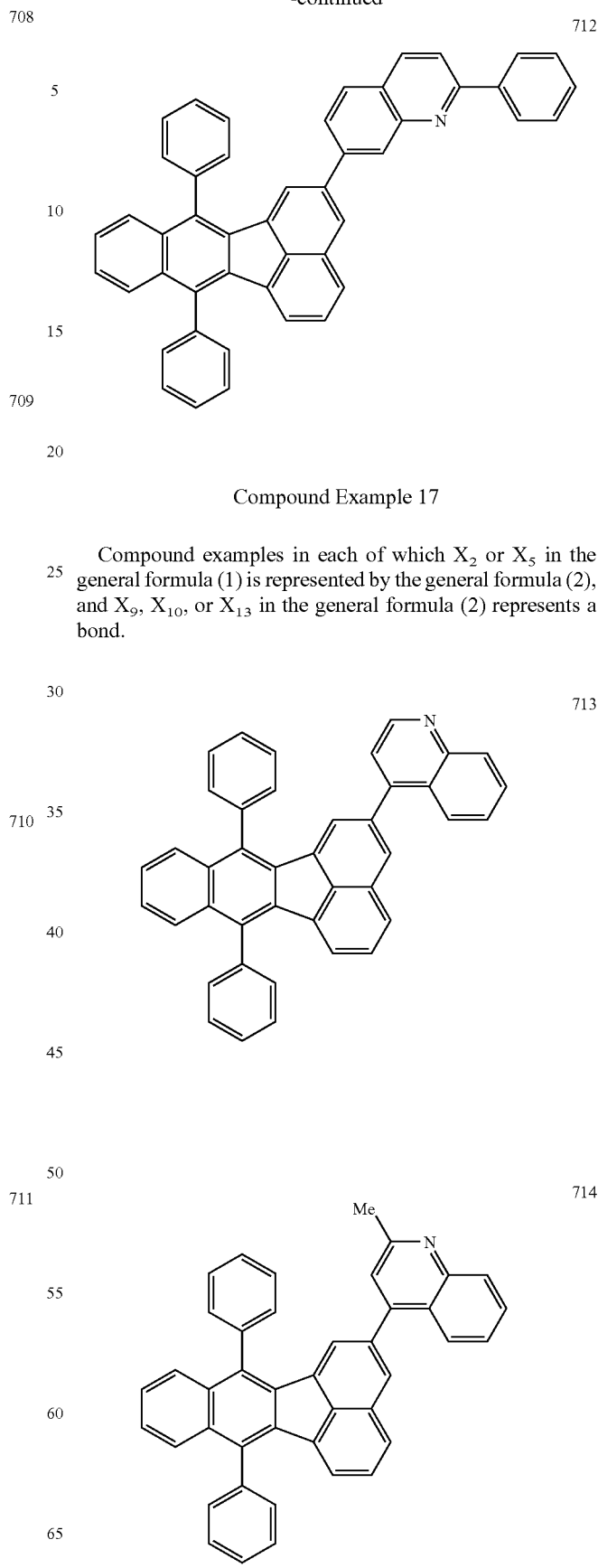
Compound Example 17
Compound examples in each of which $X_2$ or $X_5$ in the general formula (1) is represented by the general formula (2), and $X_9$, $X_{10}$, or $X_{13}$ in the general formula (2) represents a bond.

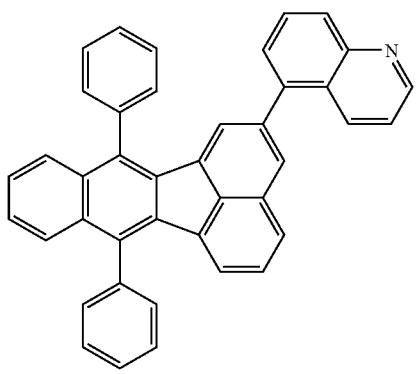
715
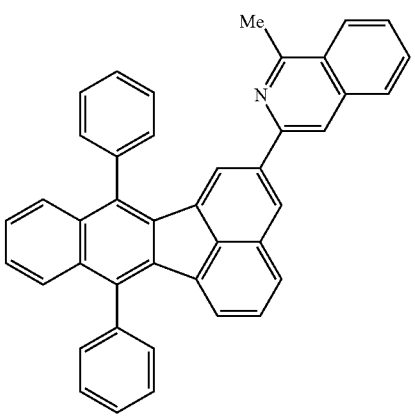
802
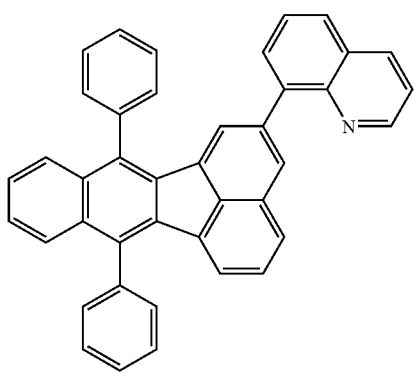
716
Compound Example 18
Compound examples in each of which $X_2$ or $X_5$ in the general formula (1) is represented by the general formula (3), and $X_{15}$, $X_{18}$, or $X_{19}$ in the general formula (3) represents a bond.
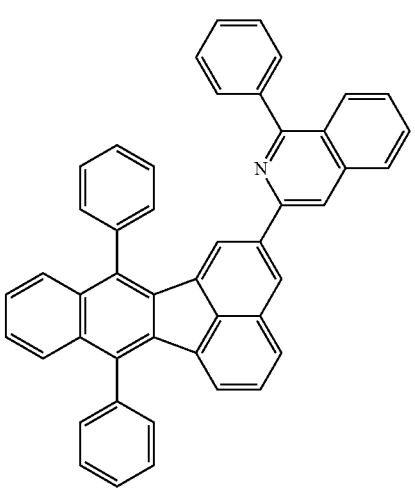
803
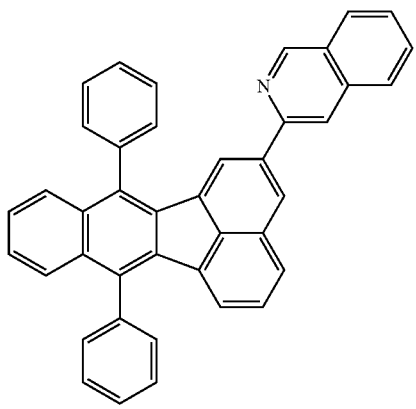
801
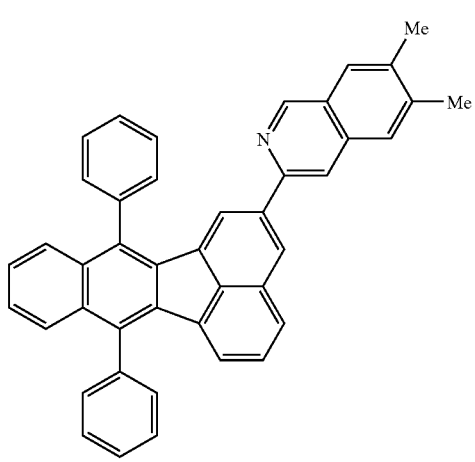
804

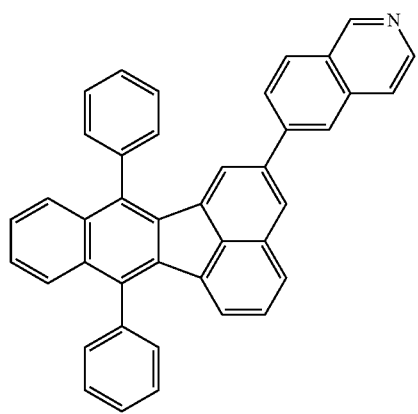
805
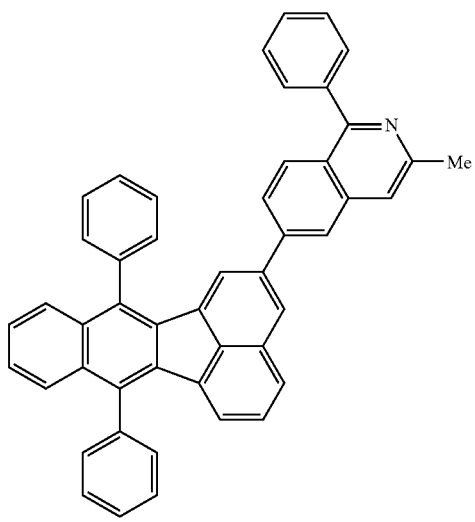
808
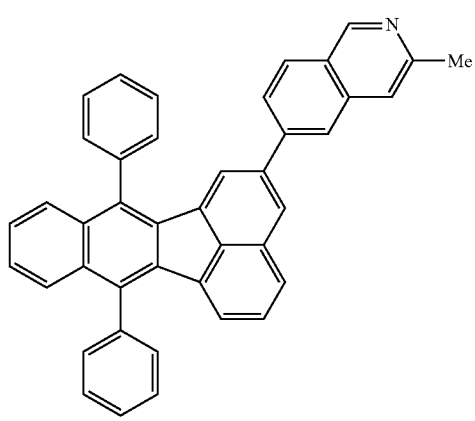
806
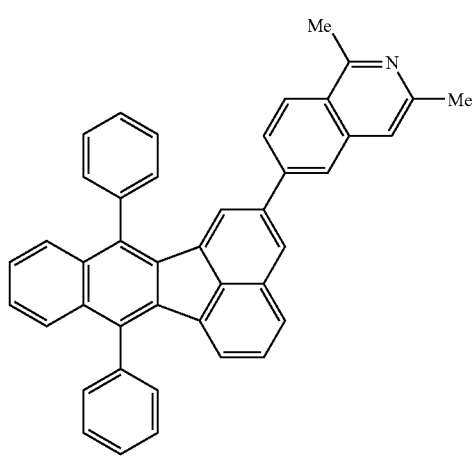
807
Compound Example 19
Compound examples in each of which $X_2$ or $X_5$ in the general formula (1) is represented by the general formula (3), and $X_{14}$, $X_{16}$, $X_{17}$, or $X_{20}$ in the general formula (3) represents a bond.
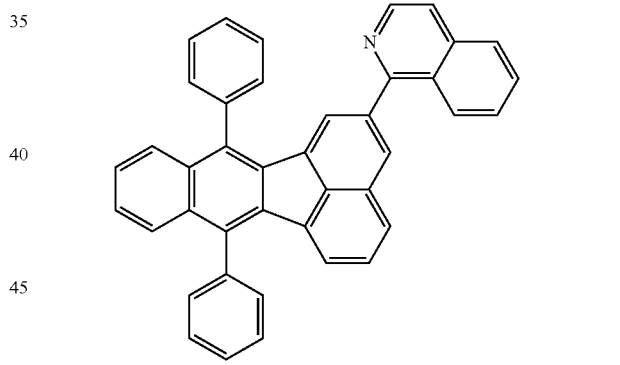
809
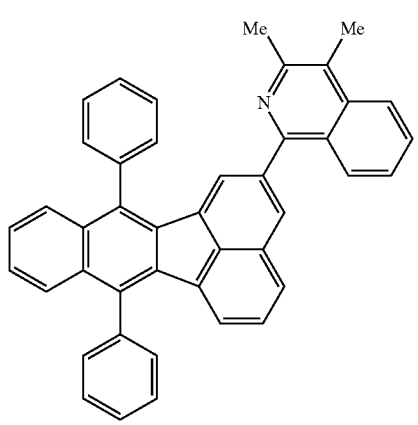
810

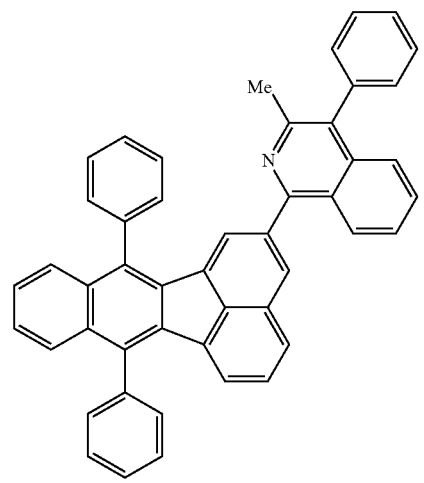
811
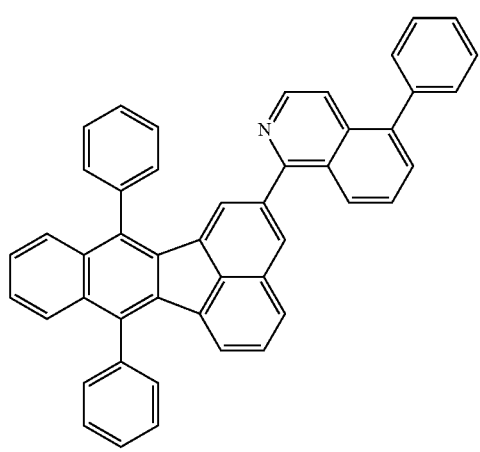
812
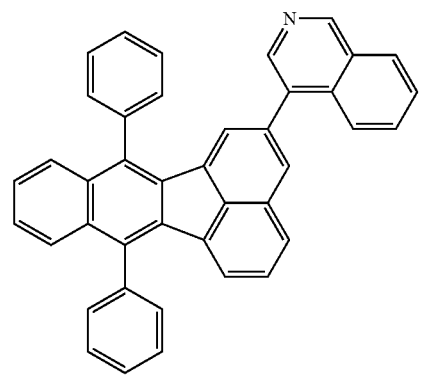
813
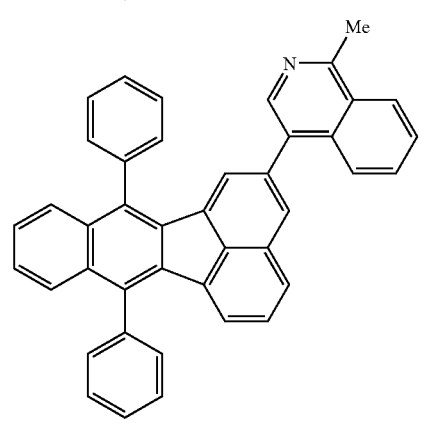
814
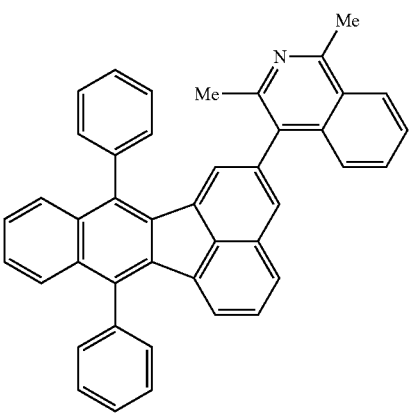
815
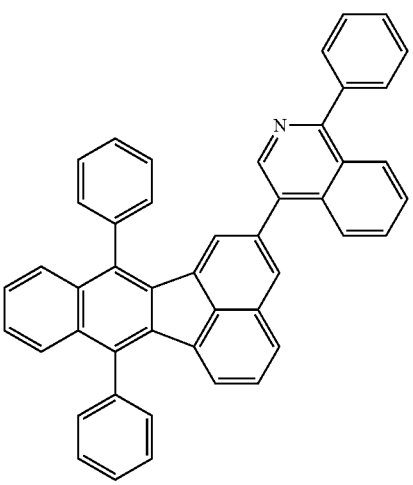
816
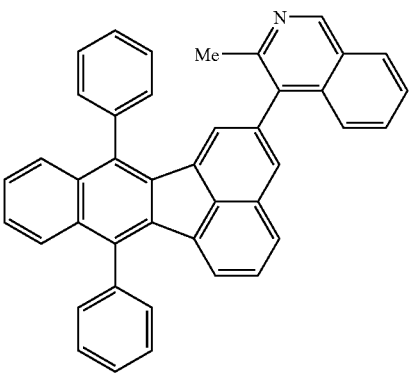
817
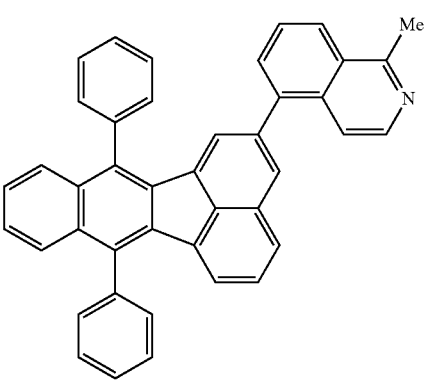
818

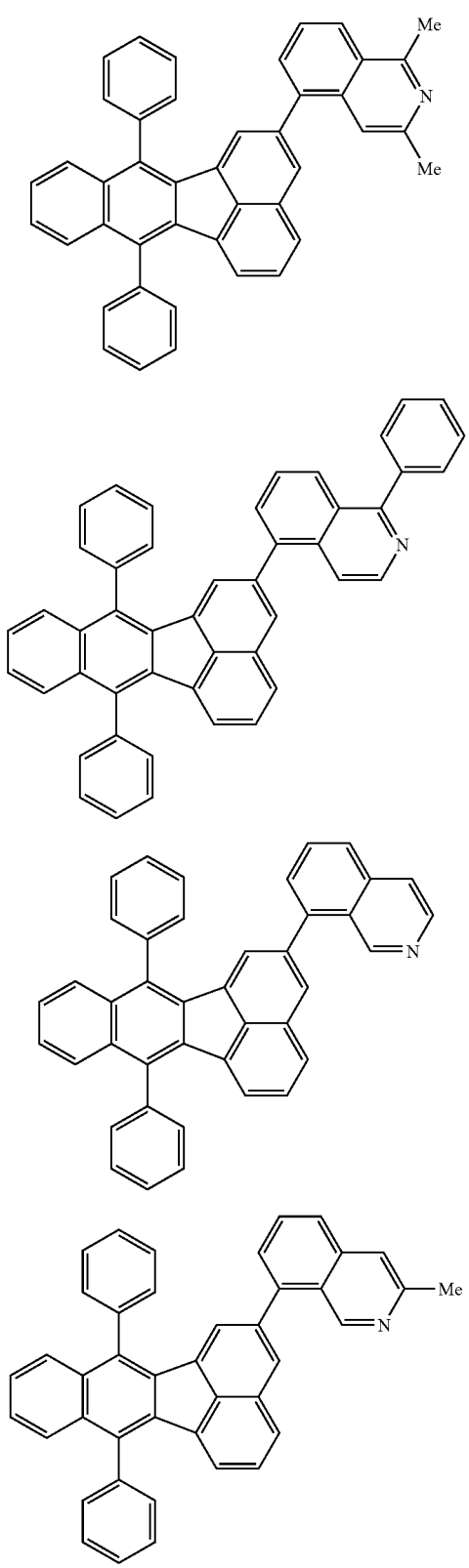

819
820
821
822

The organic light-emitting device of the present invention has a pair of electrodes including an anode and a cathode, and at least one layer containing an organic compound interposed between the pair of electrodes, in which one of the anode and the cathode is formed of a transparent or translucent electrode material. The organic light-emitting device of the present invention is preferably an electroluminescent device that emits light by applying a voltage between the pair of electrodes.

Hereinafter, the organic light-emitting device of the present invention will be described in detail with reference to the drawings.

FIG. 1 is a schematic cross-sectional view illustrating a first embodiment of the organic light-emitting device of the present invention. In the organic light-emitting device 10 shown in FIG. 1, there are sequentially provided on a substrate 1, an anode 2, a light-emitting layer 3 and a cathode 4. The configuration of the organic light-emitting device 10 is useful when the light-emitting layer 3 is composed of a compound having all of hole transporting ability, electron transporting ability and light emitting ability, or when the light-emitting layer 3 is composed of a mixture of compounds having hole transporting ability, electron transporting ability and light emitting ability, respectively.

FIG. 2 is a schematic cross-sectional view illustrating a second embodiment of the organic light-emitting device of the present invention. In the organic light-emitting device 20 shown in FIG. 2, there are sequentially provided on a substrate 1, an anode 2, a hole-transporting layer 5, an electron-transporting layer 6, and a cathode 4. The configuration of the organic light-emitting device 20 is useful when a light-emitting compound also having at least one of hole transporting ability and electron transporting ability and an organic compound having only hole-transporting ability or electron transporting ability are used in combination. Incidentally, in the organic light-emitting device 20 shown in FIG. 2, the hole-transporting layer 5 and the electron-transporting layer 6 each serve also as a light-emitting layer.

FIG. 3 is a schematic cross-sectional view illustrating a third embodiment of the organic light-emitting device of the present invention. The organic light-emitting device 30 shown in FIG. 3 is different from the organic light-emitting device 20 shown in FIG. 2 in that a light-emitting layer 3 is additionally provided between a hole-transporting layer 5 and an electron-transporting layer 6. The organic light-emitting device 30 has a configuration in which the functions of carrier transportation and light emission are separated from each other, so that organic compounds having characteristics of hole-transporting property, electron-transporting property and light-emitting property, respectively, can suitably be combined and used. Therefore, since the degree of freedom in selecting materials can significantly be increased, and further since various organic compounds having different emission wavelengths can be used, a wide variety of emission hues can be provided. Further, it also becomes possible to effectively confine carriers or excitons in the light-emitting layer 3, thereby improving the emission efficiency.

Figure 4:
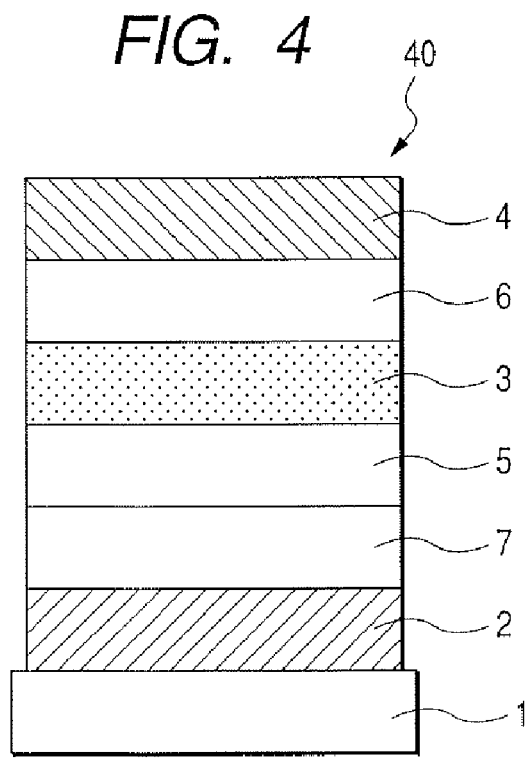
FIG. 4 is a cross-sectional view illustrating a fourth embodiment of the organic light-emitting device of the present invention.

FIG. 4 is a schematic cross-sectional view illustrating a fourth embodiment of the organic light-emitting device of the present invention. The organic light-emitting device 40 shown in FIG. 4 is different from the organic light-emitting device 30 shown in FIG. 3 in that a hole injection layer 7 is additionally provided between an anode 2 and a hole-transporting layer 5. In the organic light-emitting device 40, by additionally providing the hole injection layer 7, the adhesion between the anode 2 and the hole-transporting layer 5 is improved and the hole injection property is also improved, so that the driving voltage can be effectively reduced.

Figure 5:
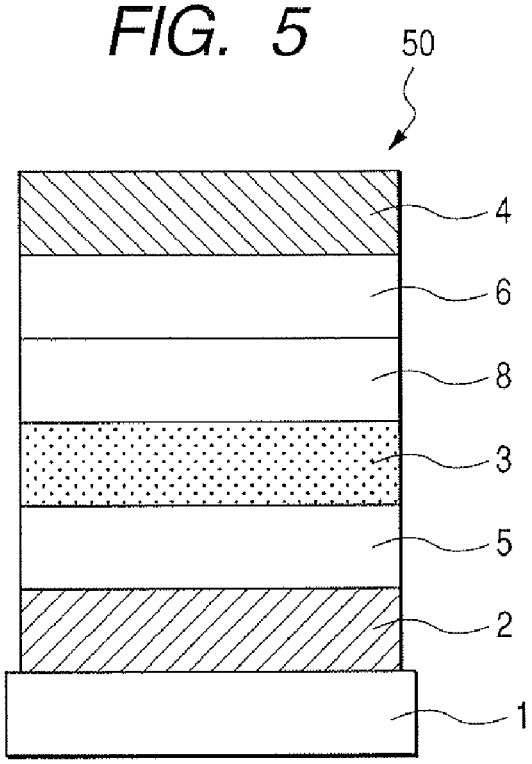
FIG. 5 is a cross-sectional view illustrating a fifth embodiment of the organic light-emitting device of the present invention.

FIG. 5 is a schematic cross-sectional view illustrating a fifth embodiment of the organic light-emitting device of the present invention. The organic light-emitting device 50 shown in FIG. 5 is different from the organic light-emitting device 30 shown in FIG. 3 in that a layer (hole/exciton blocking layer 8) for blocking holes or excitons from passing to a cathode 4 side is additionally provided between a light-emitting layer 3 and an electron-transporting layer 6. The configuration improves the emission efficiency of the organic light-emitting device 50 by using an organic compound with a significantly high ionization potential as the hole/exciton blocking layer 8.

FIGS. 1 to 5 merely show very basic device configurations and the configuration, of the organic light-emitting device according to the present invention is not limited thereto. For example, it is possible to adopt various layer structures, such as one in which an insulating layer is formed at an interface between an electrode and an organic layer, one in which an adhesive layer or an interference layer is formed, and one in which a hole-transporting layer is composed of two layers having different ionization potentials.

At least one of the benzofluoranthene compounds of the present invention is incorporated into a layer containing an organic compound such as a light-emitting layer 3, a hole-transporting layer 5, an electron-transporting layer 6, a hole injection layer 7, or a hole/exciton blocking layer 8 such as illustrated in FIGS. 1 to 5. The compound is incorporated preferably into a layer having light emitting ability, more preferably into a light-emitting layer 3. The use of the benzofluoranthene compound of the present invention can provide a device which has good emission efficiency, maintains high luminance for a long period of time, and is less susceptible to energization degradation. The benzofluoranthene compound of the present invention can be used alone, or can be used as a dopant (guest) material or a host material.

When a light-emitting layer is formed of a carrier transporting host material and a guest, the process for light emission is composed of the following several steps.

1. Transportation of electrons/holes in the light-emitting layer
2. Generation of excitons in the host
3. Transmission of excitation energy between host molecules
4. Transfer of the excitation energy from the host to the guest The desired energy transfer and light emission in the respective steps are caused in competition with various deactivation steps.

It is needless to say that in order to increase the emission efficiency of an organic light-emitting device, the emission quantum yield of a luminescent center material itself must be large. However, how high efficiency of energy transfer between hosts or between a host and a guest can be achieved is also a large problem. In addition, the cause for degradation of light emission due to energization has not been clarified yet. However, it is assumed that the degradation is related at least to a luminescent center material itself or an environmental change of a light-emitting material due to surrounding molecules. One possible cause for the degradation of light emission due to energization is degradation of light emission due to degradation of a thin-film shape of a light-emitting layer. It is believed that the degradation of the thin-film shape results from crystallization of an organic thin film due to a temperature of drive environment or heat generation at the time of driving a device. This is considered to originate from a low glass transition temperature of a material used for an organic light-emitting device, so that an organic light-emitting material is required to have a high glass transition temperature.

The benzofluoranthene compound of the present invention has a high glass transition temperature and is therefore expected to highly improve the durability of an organic light-emitting device.

The use of the benzofluoranthene compound of the present invention particularly as a host or guest for a light-emitting layer can provide a device which has good emission efficiency, maintains high luminance for a long period of time, and is less susceptible to energization degradation In addition, when the light-emitting layer is formed of a host and a guest, the host or the guest is preferably the benzofluoranthene compound of the present invention. Incidentally, the term "guest" as herein employed refers to a compound that emits mainly light in response to recombination between holes and electrons in a light-emitting region of an organic light-emitting device, and the guest is contained in another compound (host) which forms the light-emitting region.

The use of the benzofluoranthene compound of the present invention as a guest for a light-emitting layer exhibits an excellent effect. That is, by incorporating a single fused heterocyclic ring having four or less rings at a specific position of the compound, the light-emitting layer gives high-luminance light emission of a blue hue with an emission peak of 430 nm or more and 460 nm or less as well as extremely good purity at a low applied voltage and is excellent in durability.

When the benzofluoranthene compound of the present invention is used as a guest, the content of the benzofluoranthene compound based on the entire light-emitting layer is preferably 0.01 wt % or more and 80 wt % or less, more preferably 0.1 wt % or more and 30 wt % or less, and particularly preferably 0.1 wt % or more and 15 wt % or less. The guest material may be contained in the entirety of a layer formed of a host material uniformly or with a concentration gradient, or may be contained in a part of a host material layer such that the layer has a region in which no guest material is present.

In addition, when the benzofluoranthene compound of the present invention is used as a guest in a light-emitting layer, the layer preferably contains a host having an energy gap (value calculated from an optical absorption edge of UV measurement) larger than that of the guest. With such constitution, energy transfer from the guest to the host can be controlled, and the emission efficiency of the layer can be increased by light emission only from the guest.

When the benzofluoranthene compound of the present invention is used as a host, a light-emitting material which emits green light or red light is preferably used as a guest. When the benzofluoranthene compound of the present invention is used as a host, the content of the benzofluoranthene compound based on the entire light-emitting layer is preferably within the range of 50 wt % to 99.9 wt %.

The benzofluoranthene compound of the present invention may be contained only in a light-emitting layer, but may be contained also in a layer other than a light-emitting layer (such as a hole injection layer, a hole-transporting layer, an electron injection layer, an electron-transporting layer, or an electron-blocking layer) as needed.

In particular, an organic layer using the benzofluoranthene compound of the present invention is useful as a light-emitting layer, an electron-transporting layer, or a hole-transporting layer. In addition, a layer formed by, for example, a vacuum evaporation method or a solution coating method hardly undergoes crystallization or the like, and is excellent in stability over time.

The benzofluoranthene compound of the present invention is used particularly as a component of a light-emitting layer of an organic light-emitting device of the present invention. In addition, in the organic light-emitting device of the present invention, the benzofluoranthene compound of the present invention can be used not only singly but also in combination with a hitherto known low-molecular or polymer hole-transporting compound, light-emitting compound, or electron-transporting compound as needed.

Examples of such compounds will be now described below.

It is preferable that the hole injecting/transporting material facilitates injection of holes from an anode and has an excellent mobility for transporting the injected holes to a light-emitting layer. Examples of low molecular materials having the hole injecting/transporting ability include, but not limited to, a triarylamine derivative, a phenylenediamine derivative, a triazole derivative, an oxadiazole derivative, an imidazole derivative, a pyrazoline derivative, a pyrazolone derivative, an oxazole derivative, a fluorenone derivative, a hydrazone derivative, a stilbene derivative, a phthalocyanine derivative, and a porphyrin derivative. Examples of polymer materials having the hole injecting/transporting ability include, but not limited to, poly(vinylcarbazole), poly(silylene), poly(thiophen) and other conductive polymers.

As a material which is mainly involved in a light-emitting function and can be used in addition to the compound used in the organic light-emitting device of the present invention, there are included, for example, a fused ring aromatic compound (such as a naphthalene derivative, a phenanthrene derivative, a fluorene derivative, a pyrene derivative, a tetracene derivative, a coronene derivative, a chrysene derivative, a perylene derivative, a 9,10-diphenylanthracene derivative, or rubrene), a quinacridone derivative, an acridone derivative, a coumarin derivative, a pyrane derivative, Nile Red, a pyrazine derivative, a benzimidazole derivative, a benzothiazole derivative, a benzoxazole derivative, a stilbene derivative, an organometallic complex (such as an organic aluminum complex such as tris(8-quinolinolato)aluminum or an organic beryllium complex), or a polymer derivative such as a poly(phenylenevinylene) derivative, a poly(fluorene) derivative, a poly(phenylene) derivative, a poly(thienylenevinylene) derivative, or a poly(acetylene) derivative.

The electron injecting/transporting material can be arbitrarily selected from those materials which facilitate injection of electrons from a cathode and have a function of transporting the injected electrons to a light-emitting layer, and is selected in consideration of a balance with the carrier mobility of the hole-transporting material. Examples of the material having electron injecting/transporting capability include, but is not limited to, an oxadiazole derivative, an oxazole derivative, a thiazole derivative, a thiadiazole derivative, a pyrazine derivative, a triazole derivative, a triazine derivative, a perylene derivative, a quinoline derivative, a quinoxaline derivative, a fluorenone derivative, an anthrone derivative, a phenanthroline derivative and an organometallic complex.

An anode material used preferably has as large a work function as possible, and includes, for instance, an elemental metal such as gold, platinum, silver, copper, nickel, palladium, cobalt, selenium, vanadium and tungsten, an alloy thereof, and a metal oxide such as stannic oxide, zinc oxide, indium oxide, indium tin oxide (ITO) and indium zinc oxide. Further, a conductive polymer such as polyaniline, polypyrrole, polythiophene and polyphenylene sulfide can be employed. These electrode materials can be used singly or in combination. In addition, the anode may be either of a single layer configuration or of a multilayer configuration.

On the other hand, a cathode material used preferably has a low work function, and include, for instance, an elemental metal such as lithium, sodium, potassium, calcium, magnesium, aluminum, indium, ruthenium, titanium, manganese, yttrium, silver, lead, tin, and chromium. Alternatively, an alloy made of a plurality of the above metals, such as lithium-indium, sodium-potassium, magnesium-silver, aluminum-lithium, aluminum-magnesium, and magnesium-indium can also be used. A metal oxide such as indium tin oxide (ITO) can be also used. These electrode materials can be used singly or in combination. In addition, the cathode may be either of a single layer configuration or of a multilayer configuration.

A substrate used in the present invention is not particularly limited, but an opaque substrate such as a metal substrate and a ceramic substrate or a transparent substrate such as glass, quartz, and a plastic sheet is used. Further, it is also possible to employ, for a substrate, a color filter film, a fluorescent color conversion filter film and a dielectric reflection film to thereby control the emission color.

Incidentally, after a device has been produced, a protective layer or an encapsulation layer may further be provided, for the purpose of preventing contact with oxygen or moisture. Examples of such a protective layer include a diamond thin film; a film of an inorganic material such as a metal oxide and a metal nitride; a film of a polymer such as a fluororesin, poly-p-xylene, polyethylene, silicone resin, and polystyrene resin; and further a photocurable resin. Further, the produced device may also be covered with glass, a gas-impermeable film and a metal, or be packaged with a suitable encapsulation resin.

In addition, in the organic light-emitting device of the present invention, it is also possible to provide a thin film transistor (TFT) on the substrate and form a device by connecting thereto.

Further, as to the direction in which light is taken out of the device, any one of a bottom emission configuration (configuration in which light is taken out from a substrate side) and a top emission configuration (configuration in which light is taken out from a side opposite to the substrate side) may be adopted as needed.

In the organic light-emitting device of the present invention, a layer containing an organic compound of the present invention and other layers composed of an inorganic compound are formed by the below-mentioned methods. Generally, a thin film is formed by a vacuum evaporation method, an ion plating method, a sputtering method, a plasma CVD method, or a well-known coating method of applying an organic compound dissolved in a suitable solvent (such as spin coating, dipping, casting, LB method, ink jet method). Particularly, when the film is formed with the coating method, the film can be formed by additionally using a suitable binder resin.

The above described binder resin can be selected from a wide range of binding resins, and includes, for instance, polyvinylcarbazole resin, polycarbonate resin, polyester resin, polyarylate resin, polystyrene resin, ABS resin, polybutadiene resin, polyurethane resin, acrylic resin, methacrylic resin, butyral resin, polyvinylacetal resin, polyamide resin, polyimide resin, polyethylene resin, polyether sulfonic resin, diallylphthalate resin, phenolic resin, epoxy resin, silicone resin, polysulfonic resin and urea resin, but is not limited to them.

In addition, the binder resin may be singly used, or be used in combination as a copolymer. Furthermore, an additive such as a well-known plasticizer, antioxidant, and ultraviolet absorber may be further used, as needed.

In the organic light-emitting device of the present invention, the benzofluoranthene compound of the present invention is formed into a film layer) between the anode and the cathode by a vacuum evaporation method or a solution coat-

EXAMPLES

Hereinafter, the present invention will be specifically described by way of examples, but the present invention is not limited thereto.

Example 1

Production Method of Exemplified Compound No. 139

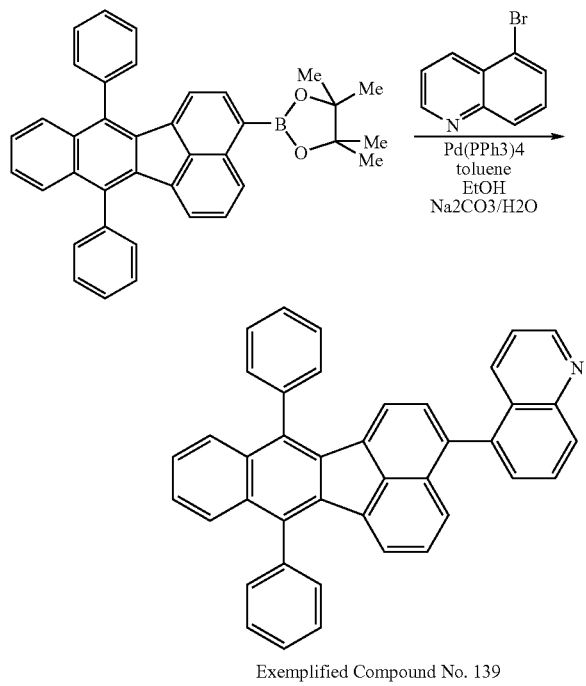

Exemplified Compound No. 139

Under nitrogen flow, the following compounds were sequentially placed in a 200 mL reaction vessel. 5-bromoquinoline: 0.26 g (0.93 mmol) 2-(7,12-diphenylbenzo[k]fluoranthene-3-yl)-4,4,5,5-tetramethyl-1,3,2-dioxaborolane: 0.50 g (0.94 mmol)

Toluene: 25 mL

Ethanol: 12 mL

10% Aqueous sodium carbonate solution: 10 mL

Tetrakis(triphenylphosphine)palladium: 0.054 g (0.05 mmol)

Next, after the reaction solution was stirred under heating and reflux for 4 hours, the solution was cooled to room temperature and added with water, and the stirring was stopped. Toluene was added to the solution, and an organic layer was separated and washed with water twice, and then the solvent was evaporated and the obtained residue was purified by column chromatography (silica gel: 76 q; mobile phase: toluene/ethyl acetate=30/1). Finally, the purified product was slurry washed with a mixed solvent of heptane/acetone to give 0.37 g of Exemplified Compound No. 139 as a pale yellow crystal.

When Exemplified Compound No. 139 was subjected to mass spectrometry by use of a mass spectrometer manufactured by Waters, 530.2 as M+was confirmed.

In addition, $^1$H-NMR of Exemplified Compound No. 139 was measured. The results are shown below.

$^1$H-NMR (CDCl$_3$): δ (ppm)=8.89 (dd, 1H, J1=4.12, J2=1.83 Hz), 8.19 (d, 1H, J=8.70 Hz), 7.85-7.77 (m, 2H), 7.73-7.52 (m, 13H), 7.42 (td, 2H, J1=6.53, J2=3.21 Hz), 7.32 (d, 1H, J=7.33 Hz), 7.23-7.17 (m, 3H), 6.71 (d, 1H, J=7.33 Hz), 6.62 (dd, 1H, J1=6.41, J2=1.37 Hz)

Figure 6:
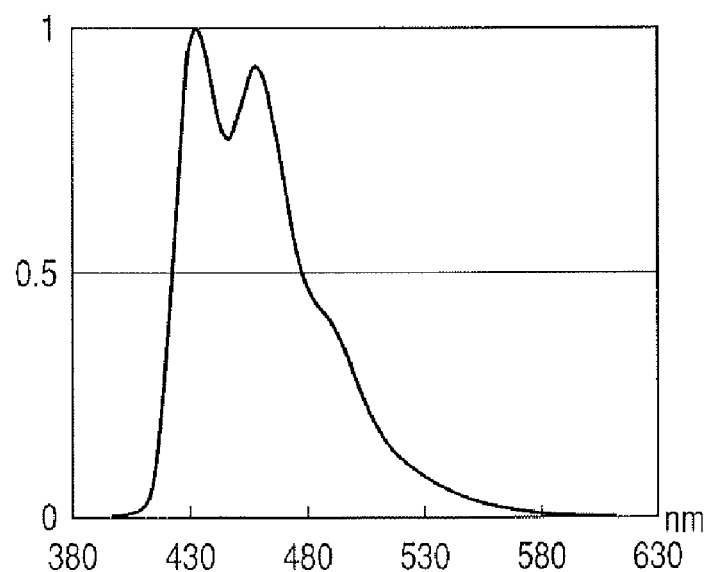
FIG. 6 is a graphical representation illustrating the PL spectrum of a solution of Exemplified Compound No. 139 in toluene ($1.0 \times 10^{-5}$ mol/L).

Further, when a photoluminescence (PL) spectrum of a solution of Exemplified Compound No. 139 in toluene (1.0× 10$^{-5}$ mol/L) was measured, the spectrum illustrated in FIG. 6 was obtained. The solution showed a blue emission spectrum having an emission peak at 433 nm, a full width at half maximum of 55 nm, and excellent color purity.

Further, each of the following exemplified compounds can be synthesized by following the same procedure as in Example 1 with the exception that each of the following compounds is used instead of 5-bromoquinoline of Example 1.

(Exemplified Compound 119): 3-bromoquinoline (Exemplified Compound 121): 6-bromo-2-methylquinoline (Exemplified Compound 126): 7-bromo-2-methylquinoline (Exemplified Compound 130): 4-bromo-2-methylquinoline (Exemplified Compound 136): 4-chloro-2-phenylquinoline (Exemplified Compound 211): 4-bromoisoquinoline (Exemplified Compound 225): 6-bromoisoquinoline (Exemplified Compound 229): 7-bromoisoquinoline (Exemplified Compound 401): 9-bromo-acridine (Exemplified Compound 601): 5-bromoquinoxaline (Exemplified Compound 602): 5-bromo-2,3-dimethylquinoxaline (Exemplified Compound 607): 2-bromoquinoxaline (Exemplified Compound 610): 6-bromo-2-phenyloxazolo[4,5-b]pyridine

Example 2

Production Method of Exemplified Compound No. 129

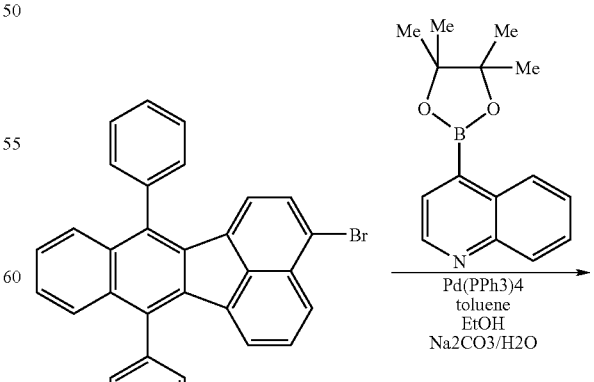

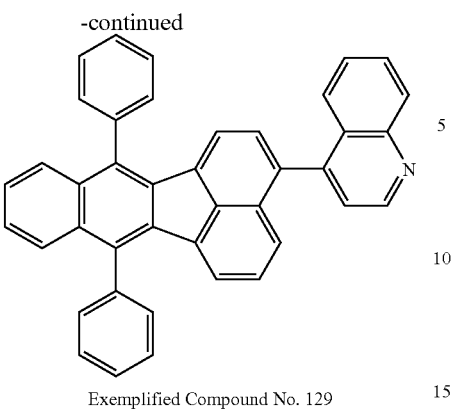

Exemplified Compound No. 129

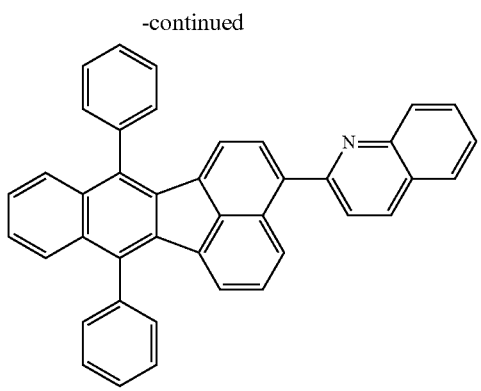

Exemplified Compound No. 101

By performing a synthesis following the same procedure as in Example 1 with the exception that 0.26 g (1.13 mmol) of 4-(4,4,5,5-tetramethyl-1,3,2-dioxaborolan-2-yl)quinoline was used instead of 0.26 g (0.93 mmol) of 5-bromoquinoline in Example 1 and 0.50 g (1.03 mmol) of 3-bromo-7,12-diphenylbenzo[k]fluoranthene was used instead of 0.50 g (0.94 mmol) of 2-(7,12-diphenylbenzo[k]fluoranthen-3-yl)-4,4,5,5-tetramethyl-1,3,2-dioxaborolane in Example 1, 0.32 g of Exemplified Compound No. 129 was obtained as a pale yellow crystal.

When Exemplified Compound No. 129 was subjected to mass spectrometry by use of a mass spectrometer manufactured by Waters, 530.2 as M+ was confirmed.

In addition, $^1$H-NMR of Exemplified Compound No. 129 was measured. The results are shown below.

$^1$H-NMR (CDCl$_3$): δ (ppm)=8.98 (d, 1H, J=4.57 Hz), 8.18 (d, 1H, J=8.23 Hz), 7.71-7.52 (m, 13H), 7.42 (td, 2H, J1=6.52, J2=3.35 Hz), 7.38-7.32 (m, 3H), 7.25-7.13 (m, 3H), 6.71 (d, 1H, J=6.86 Hz), 6.61 (d, 1H, J=6.86 Hz)

Figure 7:
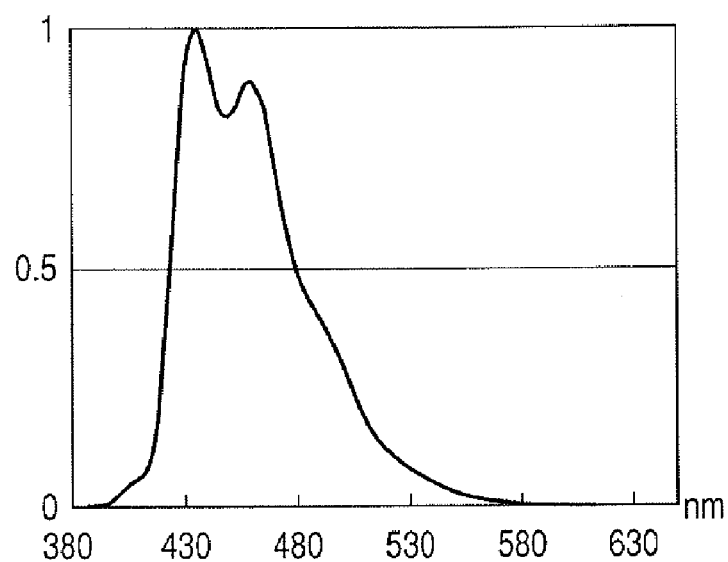
FIG. 7 is a graphical representation illustrating the PL spectrum of a solution of Exemplified Compound No. 129 in toluene ($1.0 \times 10^{-5}$ mol/L).

Further, when a PL spectrum of a solution of Exemplified Compound No. 129 in toluene (1.0×10$^{-5}$ mol/L) was measured, the spectrum illustrated in FIG. 7 was obtained. The solution showed a blue emission spectrum having an emission peak at 436 nm, a full width at half maximum of 56 nm, and excellent color purity.

Example 3

Production Method of Exemplified Compound No. 101

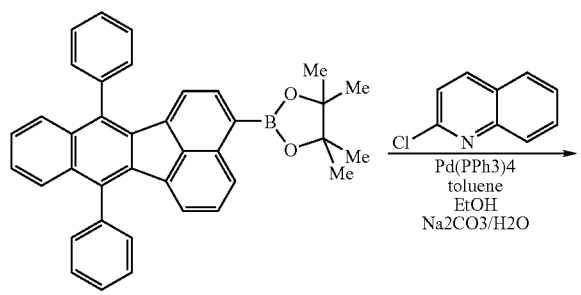

By performing a synthesis following the same procedure as in Example 1 with the exception that 0.15 g (0.92 mmol) of 2-chloroquinoline was used instead of 0.26 g (0.93 mmol) of 5-bromoquinoline of Example 1, 0.41 g of Exemplified Compound No. 101 was obtained as a yellow crystal.

When Exemplified Compound No. 101 was subjected to mass spectrometry by use of a mass spectrometer manufactured by Waters, 530.2 as M+ was confirmed.

In addition, $^1$H-NMR of Exemplified Compound No. 101 was measured. The results are shown below.

$^1$H-NMR (CDCl$_3$): δ (ppm)=8.25 (d, 1H, J=8.69 Hz), 8.22 (d, 1H, J=8.23 Hz), 8.19 (d, 1H, J=8.69 Hz), 7.87 (d, 1H, J=7.32 Hz), 7.76-7.74 (m, 2H), 7.70-7.55 (m, 14H), 7.40 (dq, 2H, J1=6.63, J2=3.32 Hz), 7.35 (dd, 1H, J1=8.23, J2=7.32 Hz), 6.72 (d, 1H, J=7.32 Hz), 6.65 (d, 1H, J=6.86 Hz)

Figure 8:
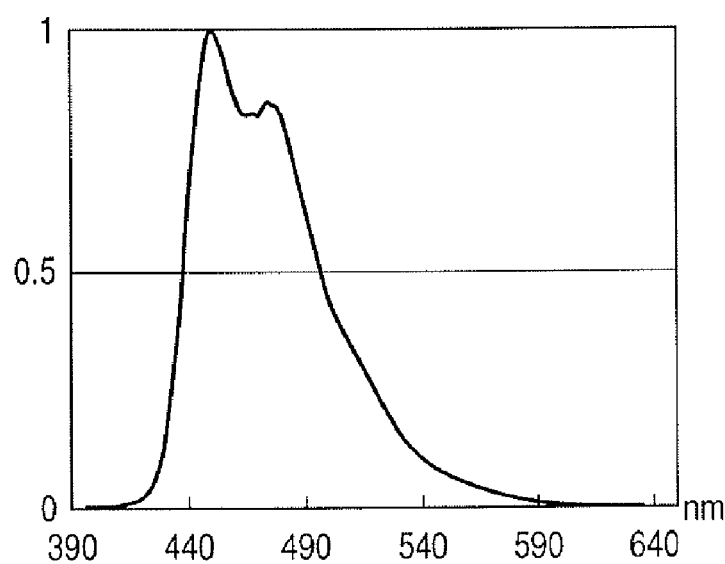
FIG. 8 is a graphical representation illustrating the PL spectrum of a solution of Exemplified Compound No. 101 in toluene ($1.0 \times 10^{-5}$ mol/L).

Further, when a PL spectrum of a solution of Exemplified Compound No. 101 in toluene (1.0×10$^{-5}$ mol/L) was measured, the spectrum illustrated in FIG. 8 was obtained. The solution showed a blue emission spectrum having an emission peak at 450 nm, a full width at half maximum of 59 nm, and excellent color purity.

Further, each of the following exemplified compounds can be synthesized by following the same procedure as in Example 3 with the exception that each of the following compounds is used instead of 2-chloroquinoline of Example 3.

(Exemplified Compound 201): 1-bromo-isoquinoline (Exemplified Compound 206): 1-chloro-5-phenylisoquinoline (Exemplified Compound 208): 1-chloro-3-phenylisoquinoline (Exemplified Compound 221): 3-bromoisoquinoline (Exemplified Compound 222): 3-bromo-1-methylisoquinoline Further, Exemplified Compound No. 701 can be synthesized by following the same procedure as in Example 3 with the exception that 2-(7,12-diphenylbenzo[k]fluoranthen-2-yl)-4,4,5,5-tetramethyl-1,3,2-dioxaborolane is used instead of 2-(7,12-diphenylbenzo[k]fluoranthen-3-yl)-4,4,5,5-tetramethyl-1,3,2-dioxaborolane of Example 3.

Example 4

Production Method of Exemplified Compound No. 301

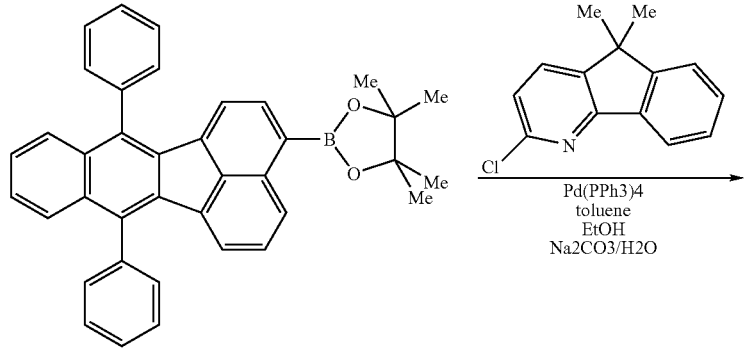

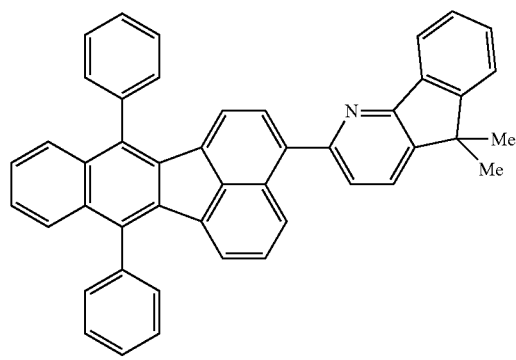

Exemplified Compound No. 301

By performing a synthesis following the same procedure as in Example 1 with the exception that 0.22 g (0.94 mmol) of 2-chloro-5,5-dimethyl-5H-indeno[1,2-b]pyridine was used instead of 0.26 g (0.93 mmol) of 5-bromoquinoline of Example 1, 0.38 g of Exemplified Compound No. 301 was obtained as a yellow crystal.

When Exemplified Compound No. 301 was subjected to mass spectrometry by use of a mass spectrometer manufactured by Waters, 597.2 as M+ was confirmed.

In addition, $^1$H-NMR of Exemplified Compound No. 301 was measured. The results are shown below.

$^1$H-NMR (CDCl$_3$): δ (ppm)=8.25 (d, 1H, J=8.69 Hz), 8.08 (dd, 1H, J1=6.40, J2=2.29 Hz), 7.78 (d, 1H, J=7.78 Hz), 7.71-70.58 (m, 13H), 7.51-7.48 (m, 2H), 7.43-7.39 (m, 4H), 7.34 (dd, 1H, J1=8.23, J2=7.32 Hz), 6.71 (d, 1H, J=7.32 Hz), 6.64 (d, 1H, J=6.86 Hz)

Figure 9:
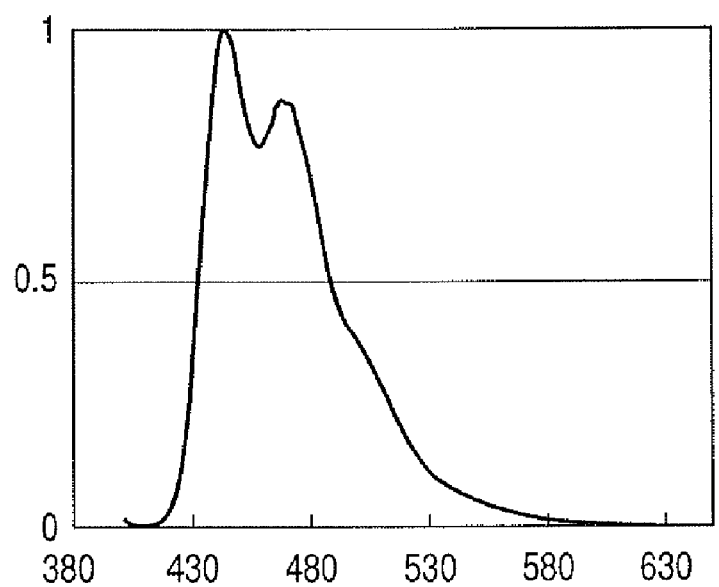
FIG. 9 is a graphical representation illustrating the PL spectrum of a solution of Exemplified Compound No. 301 in toluene ($1.0 \times 10^{-5}$ mol/L).

Further, a PL spectrum of a solution of Exemplified Compound No. 301 in toluene ($1.0 \times 10^{-5}$ mol/L) was measured. As a result, the spectrum illustrated in FIG. 9 was obtained. The solution showed a blue emission spectrum having an emission peak at 445 nm, a full width at half maximum of 57 nm, and excellent color purity.

Further, each of the following exemplified compounds can be synthesized by following the same procedure as in Example 4 with the exception that each of the following compounds is used instead of 2-chloro-5,5-dimethyl-5H-indeno[1,2-b]pyridine of Example 4.

(Exemplified Compound 305): 4-chloro-5,5-dimethyl-5H-indeno[1,2-b]pyridine (Exemplified Compound 311): 8-bromo-5,5-dimethyl-5H-indeno[1,2-b]pyridine (Exemplified Compound 316): 8-bromo-5,5-dimethyl-2-phenyl-5H-indeno[1,2-b]pyridine (Exemplified Compound 317): 7-bromo-5,5-dimethyl-5H-indeno[1,2-b]pyridine (Exemplified Compound 319): 7-bromo-2,5,5-trimethyl-5H-indeno[1,2-b]pyridine

Example 5

Production Method of Exemplified Compound No. 501

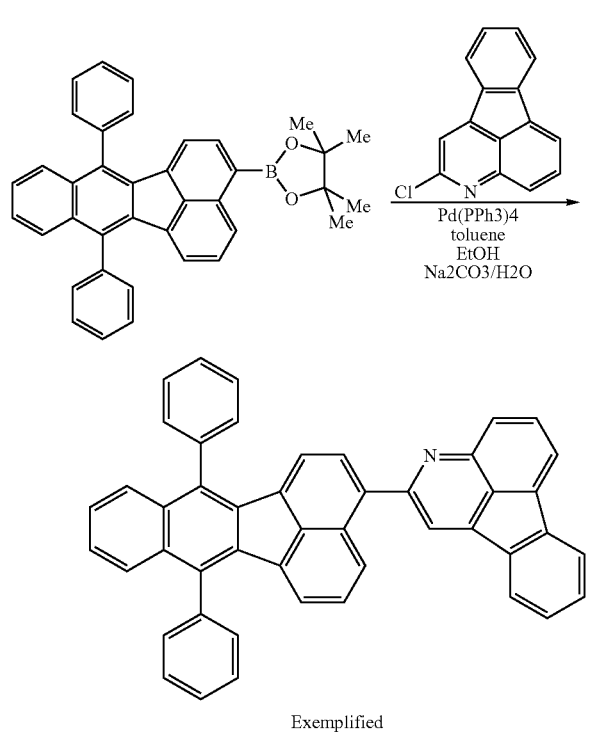

Exemplified Compound No. 501

(1) Synthesis of 2-chloroindeno[1,2,3-de]quinoline

By following the procedure described in Journal of Medicinal Chemistry 1990, 42, 1556-1575, 11.4 g of 2-chloroindeno[1,2,3-de]quinoline was synthesized according to the following synthesis scheme.

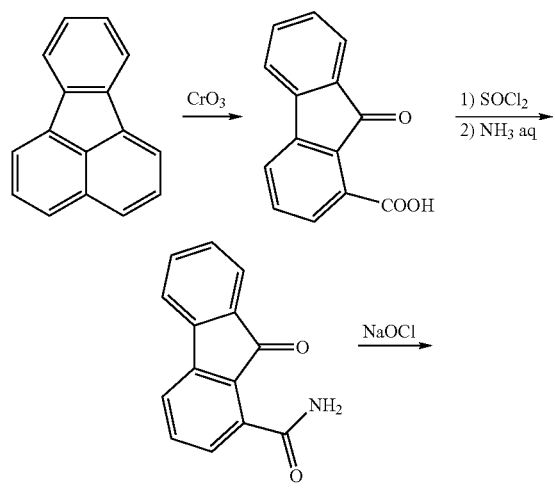

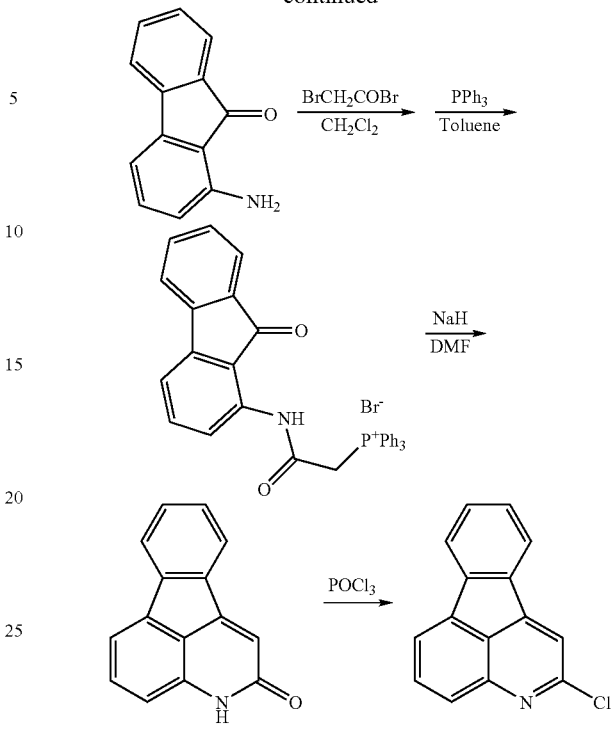

(2) Synthesis of Exemplified Compound No. 501

By following the same procedure as in Example 1 with the exception that 0.23 g (0.94 mmol) of 2-chloroindeno[1,2,3-de]quinoline synthesized according to the above synthesis scheme was used instead of 0.26 g (0.93 mmol) of 5-bromoquinoline of Example 1, 0.35 g of Exemplified Compound No. 501 was obtained as a yellow crystal.

When Exemplified Compound No. 501 was subjected to mass spectrometry by use of a mass spectrometer manufactured by Waters, 605.1 as M+ was confirmed.

In addition, $^1$H-NMR of Exemplified Compound No. 501 was measured. The results are shown below.

$^1$H-NMR (CDCl$_3$): δ (ppm)=8.19 (d, 1H, J=8.23 Hz), 8.08 (s, 1H), 8.05 (d, 1H, J=8.23 Hz), 7.90-7.88 (m, 3H), 7.78 (dd, 1H, J1=8.46, J2=7.09 Hz), 7.73-7.55 (m, 13H), 7.48 (td, 1H, J1=7.55, J2=1.22 Hz), 7.44-7.34 (m, 4H), 6.74 (d, 1H, J=7.32 Hz), 6.66 (d, 1H, J=7.32 Hz)

Figure 10:
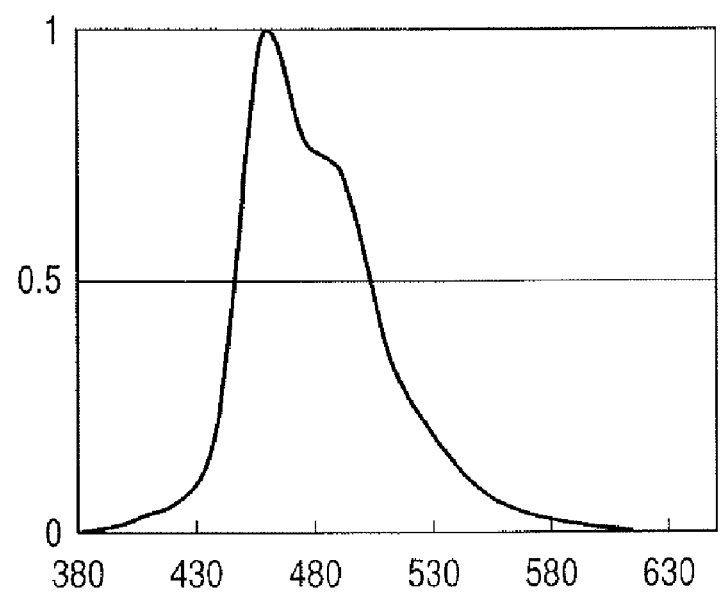
FIG. 10 is a graphical representation illustrating the PL spectrum of a solution of Exemplified Compound No. 501 in toluene ($1.0 \times 10^{-6}$ mol/L).

Further, when a PL spectrum of a solution of Exemplified Compound No. 501 in toluene (1.0×10$^{-6}$ mol/L) was measured, the spectrum illustrated in FIG. 10 was obtained. The solution showed a blue emission spectrum having an emission peak at 462 nm, a full width at half maximum of 58 nm, and excellent color purity.

Further, each of the following exemplified compounds can be synthesized by following the same procedure as in Example 5 with the exception that each of the following compounds is used instead of 2-chloroindeno[1,2,3-de]quinoline of Example 5.

(Exemplified Compound 509): indeno[1,2,3-de]quinoline-4-yltrifluoromethanesulfonate
(Exemplified Compound 510): 2-methyl-indeno[1,2,3-de]quinolin-4-yltrifluoromethanesulfonate
(Exemplified Compound 515): 5-chloro-indeno[1,2,3-de]quinoline
(Exemplified Compound 531): 9-bromo-indeno[1,2,3-de]quinoline

Example 6

An organic light-emitting device having a structure shown in FIG. 4 was produced by the following method.

On a glass substrate (substrate 1), indium tin oxide (ITO) was formed into a film in a thickness of 120 nm as an anode 2 by a sputtering method. Next, the glass substrate having the ITO film formed thereon was ultrasonically cleaned sequentially with acetone and isopropyl alcohol (IPA), subsequently cleaned with pure water, dried, and further cleaned with UV/ozone. The glass substrate thus treated was used as a transparent conductive support substrate.

Next, a solution of Compound 1 represented by the following formula as a hole-transporting material in chloroform (concentration: 0.1 wt %) was prepared, and was dropped onto the above transparent conductive support. After the dropping, the substrate was subjected to spin coating by being rotated initially at 500 RPM for 10 seconds and then at 1,000 RPM for 40 seconds, whereby a film was formed. After that, the film was dried in a vacuum oven at 80° C. for 10 minutes so that the solvent in the film was completely removed, whereby a hole injection layer 7 was formed.

Compound 1

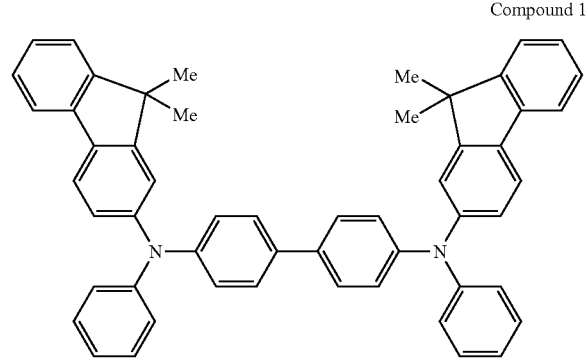

Next, on the hole injection layer 7, Compound 2 represented by the following formula was deposited into a film in a thickness of 15 nm by a vacuum evaporation method to form the hole-transporting layer 5.

Compound 2

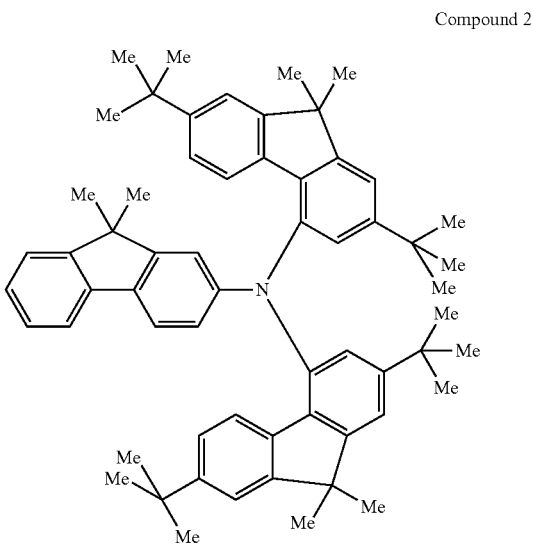

Then, on the hole-transporting layer 5, Exemplified Compound No. 139 as a guest and Compound 3 as a host represented by the following formula were coevaporated in a thickness of 30 nm to provide a light emitting layer 3. At this time, the content of Exemplified Compound No. 139 in the entire light-emitting layer was set to 5 wt %. In addition, the light-emitting layer 3 was formed under the conditions of a degree of vacuum during evaporation of $1.0 \times 10^{-4}$ Pa and a film formation rate of 0.1 to 0.2 nm/sec. Incidentally, Exemplified Compound No. 139 had an energy gap of 2.87 eV, and Compound 3 represented by the following formula had an energy gap of 3.06 eV.

Compound 3

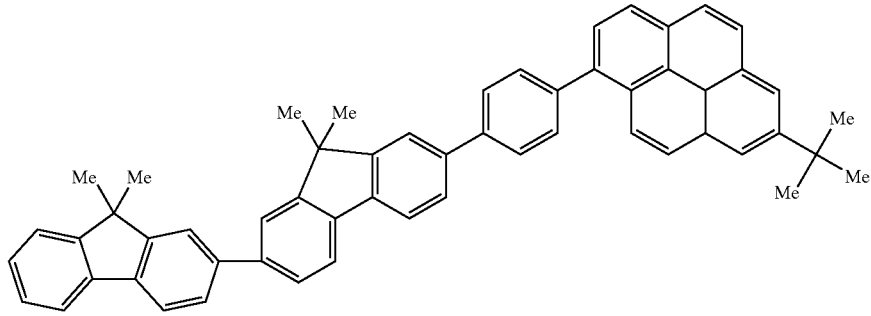

Further, on the light-emitting layer 3, a film of 2,9-bis[2-(9,9'-dimethylfluorenyl)]-1,10-phenanthroline was deposited in a thickness of 30 nm by a vacuum evaporation method to form an electron-transporting layer 6. Incidentally, the electron-transporting layer 6 was formed under the conditions of a degree of vacuum during evaporation of $1.0 \times 10^{-4}$ Pa and a film formation rate of 0.1 to 0.2 nm/sec.

Next, on the electron-transporting layer 6, a film of lithium fluoride (LiF) was deposited in a thickness of 0.5 nm by a vacuum evaporation method under the conditions of a degree of vacuum during evaporation of $1.0\text{-}10^{-4}$ Pa and a film formation rate of 0.01 nm/sec. Finally, on the LiF film, an aluminium film having a thickness of 100 nm was formed by a vacuum evaporation method under the conditions of a degree of vacuum during evaporation of $1.0 \times 10^{-4}$ Pa and a film formation rate of 0.5 to 1.0 nm/sec. Thus, the organic light-emitting device was produced.

The resultant organic light-emitting device was covered with a protective glass plate in a dry air atmosphere so that the device was not degraded through adsorbing moisture, and was encapsulated with an acrylic resin adhesive.

A voltage of 4 V was applied to the device thus obtained with the ITO electrode (anode 2) being connected to a positive electrode of a power supply and the Al electrode (cathode 4) being connected to a negative electrode of the power supply. As a result, the device was observed to emit light with a current efficiency of 5.4 cd/A and an emission efficiency of 4.3 lm/W. In addition, the device was observed to emit blue light of good color purity with CIE chromaticity coordinates of x=0.15 and y=0.12.

Further, when a voltage was applied to the device in a nitrogen atmosphere at a current density of 30 mA/cm$^2$ for 100 hours, the luminance was degraded from 1,543 cd/m$^2$ to 920 cd/m$^2$, but the device was confirmed to satisfactorily continue to emit light.

Example 7

A device was produced by following the same procedure as in Example 6 with the exception that Exemplified Compound No. 129 described above was used instead of Exemplified Compound No. 139 used in Example 6 above. Incidentally, Exemplified Compound No. 129 had an energy gap of 2.87 eV.

A voltage of 4 V was applied to the thus produced device. As a result, the device was observed to emit light with a current efficiency of 4.5 cd/A and an emission efficiency of 3.6 lm/W. In addition, the device was observed to emit blue light of good color purity with CIE chromaticity coordinates of x=0.14 and y=0.12.

Further, when a voltage was applied to the device in a nitrogen atmosphere at a current density of 30 mA/cm$^2$ for 100 hours, the luminance of the device was degraded from 1,373 cd/m$^2$ to 965 cd/m$^2$, but the device was confirmed to satisfactorily continue to emit light.

Example 8

A device was produced by following the same procedure as in Example 6 with the exception that Exemplified Compound No. 101 described above was used instead of Exemplified Compound No. 139 used in Example 6 above. Incidentally, Exemplified Compound No. 101 had an energy gap of 2.79 eV.

A voltage of 4 V was applied to the thus produced device. As a result, the device was observed to emit light with a current efficiency of 6.2 cd/A and an emission efficiency of 4.91 lm/W. In addition, the device was observed to emit blue light of good color purity with CIE chromaticity coordinates of x=0.14 and y=0.18. In other words, the device was observed to emit blue light with a good color purity.

Further, a voltage was applied to the device in a nitrogen atmosphere at a current density of 30 mA/cm$^2$ for 100 hours. As a result, the luminance of the device was degraded from 1,803 cd/m$^2$ to 1,482 cd/m$^2$, but the device was confirmed to satisfactorily continue to emit light.

Comparative Example 1

A device was produced by following the same procedure as in Example 6 with the exception that Compound 4 represented by the structure shown below was used instead of Exemplified Compound No. 139 used in Example 6 above. Incidentally, Compound 4 had an energy gap of 2.94 eV.

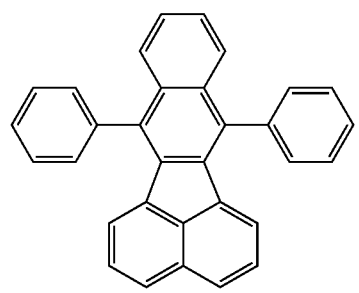

Compound 4

A voltage of 4 V was applied to the thus produced device. As a result, the device was observed to emit light with a current efficiency of 2.4 cd/A and an emission efficiency of 1.9 lm/W.

Further, when a voltage was applied to the device in a nitrogen atmosphere for 20 hours such that the current density was kept at 30 mA/cm$^2$, an initial luminance of 840 cd/m$^2$ was degraded down to 406 cd/m$^2$, which was less than half of the initial luminance, in 20 hours.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-349579, filed Dec. 26, 2006, which is hereby incorporated by reference herein in its entirety.

The invention claimed is:

1. A benzofluoranthene compound represented by the following general formula (1):

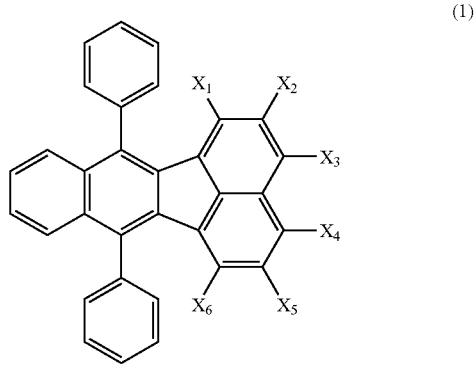

(1)

wherein one of $X_3$ and $X_4$ represents a substituted or unsubstituted fused heterocyclic group, and the other of $X_3$ and $X_4$, $X_1$, $X_2$, $X_5$, and $X_6$ each represent a hydrogen atom, and wherein the fused heterocyclic group is a substituent represented by the following general formula (2):

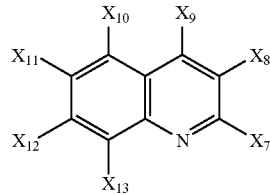

wherein one of $X_7$, $X_9$, and $X_{10}$ represents a bond, and the others of $X_7$, $X_9$, and $X_{10}$, $X_8$, $X_{11}$, $X_{12}$, and $X_{13}$ each represent a hydrogen atom, or by the following general formula (4):

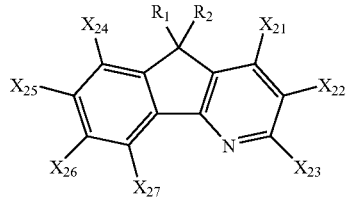

wherein $X_{23}$ represents a bond; $X_{21}$, $X_{22}$, $X_{24}$, $X_{25}$, $X_{26}$, and $X_{27}$ each represent, independently of one another, a hydrogen atom, an alkyl group or a phenyl group; and $R_1$ and $R_2$ each represent, independently of one another, a methyl group, an ethyl group, an n-propyl group, an iso-propyl group, an n-butyl group, an iso-butyl group, a sec-butyl group, and a tert-butyl group, or by the following general formula (6):

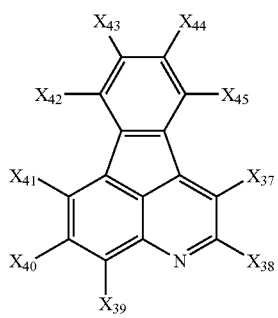

wherein $X_{38}$ represents a bond; $X_{37}$, $X_{39}$, $X_{40}$, $X_{41}$, $X_{42}$, $X_{43}$, $X_{44}$, and $X_{45}$ each represent, independently of one another, a hydrogen atom, an alkyl group or a phenyl group; and the alkyl group is any one of a methyl group, an ethyl group, an n-propyl group, an iso-propyl group, an n-butyl group, an iso-butyl group, a sec-butyl group, and a tert-butyl group.

2. A benzofluoranthene compound represented by any one of the following structural formulae:

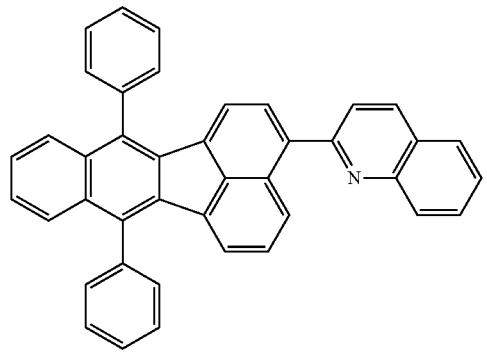

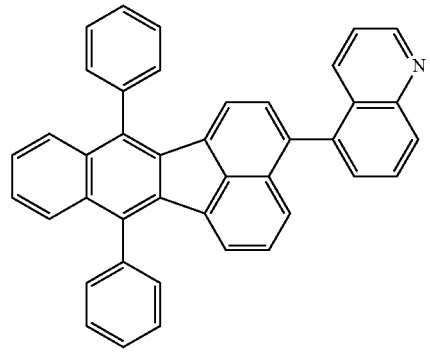

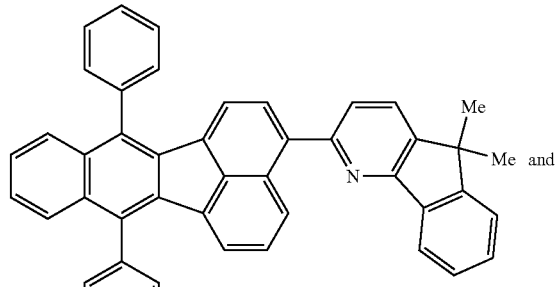

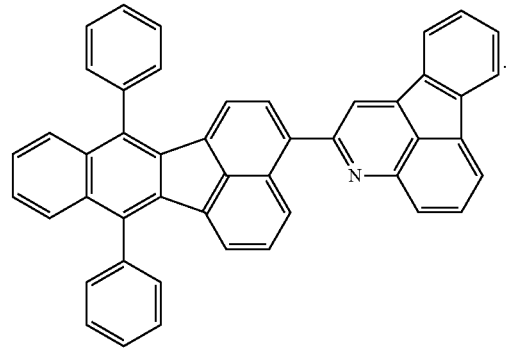

3. An organic light-emitting device comprising:
a pair of electrodes including an anode and a cathode, one of which is formed of a transparent or translucent electrode material; and
an organic compound layer disposed between the pair of electrodes,
wherein the organic compound layer comprises the benzofluoranthene compound set forth in claim 1 or 2.

4. The organic light-emitting device according to claim 3, wherein the organic compound layer is a light-emitting layer.

5. The organic light-emitting device according to claim 4, wherein the light-emitting layer is constituted of a host and a guest.

6. The organic light-emitting device according to claim 5, wherein the host is a compound represented by the following structural formula:
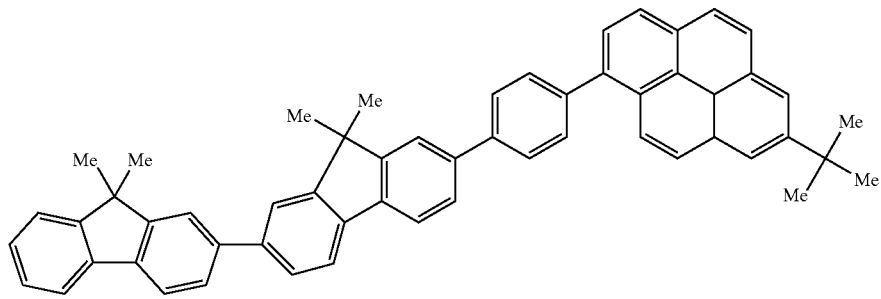
and the guest is a compound represented by any one of the following structural formulae:
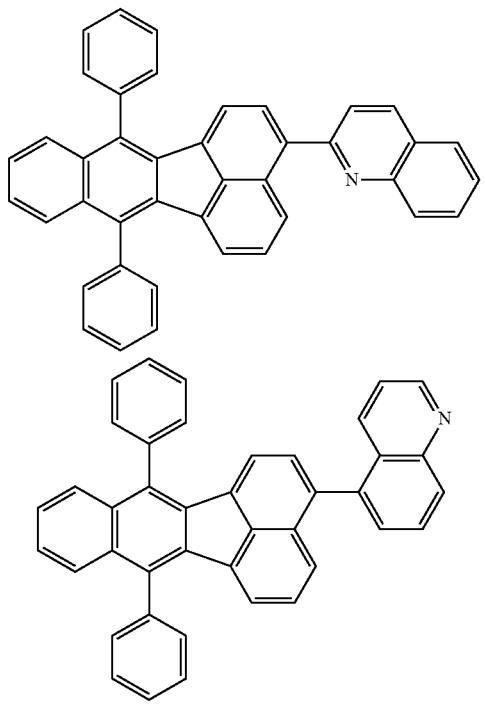
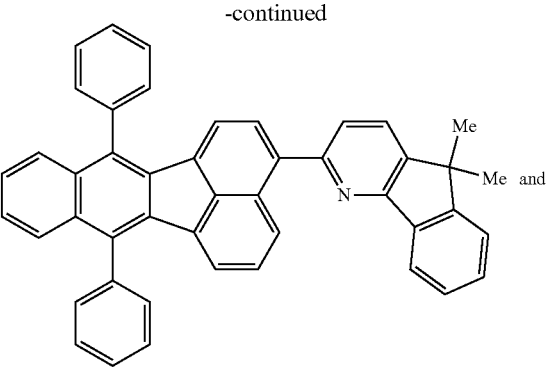
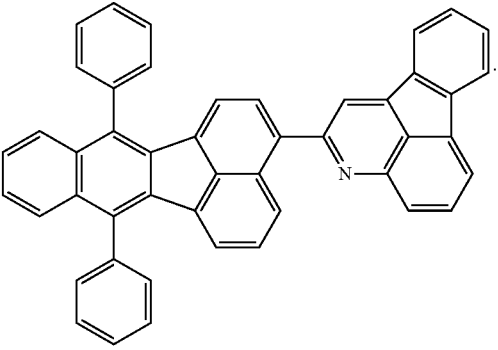
* * * * *